United States Patent
Koliatsos et al.

(10) Patent No.: US 12,364,681 B2
(45) Date of Patent: Jul. 22, 2025

(54) COMBINED MAPK AND NAMPT INHIBITION FOR TREATMENT OF NEURON DEGENERATION

(71) Applicant: The Johns Hopkins University, Baltimore, MD (US)

(72) Inventors: Vassilis E. Koliatsos, Baltimore, MD (US); Athanasios Alexandris, Baltimore, MD (US); Jiwon Ryu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/570,809

(22) Filed: Jan. 7, 2022

(65) Prior Publication Data

US 2022/0218662 A1    Jul. 14, 2022

Related U.S. Application Data

(60) Provisional application No. 63/135,149, filed on Jan. 8, 2021.

(51) Int. Cl.
*A61K 31/404* (2006.01)
*A61K 31/4406* (2006.01)
(Continued)

(52) U.S. Cl.
CPC ........ *A61K 31/404* (2013.01); *A61K 31/4406* (2013.01); *A61K 31/4409* (2013.01);
(Continued)

(58) Field of Classification Search
CPC .............. A61K 31/404; A61K 31/4406; A61K 31/4409; A61K 31/4439; A61K 31/4545; A61K 31/506; A61K 31/706; A61K 31/553; A61K 45/06; A61K 2300/00; A61P 25/02; A61P 25/28

See application file for complete search history.

(56) References Cited

U.S. PATENT DOCUMENTS

| | | |
|---|---|---|
| 2006/0002914 A1 | 1/2006 | Milbrandt et al. |
| 2013/0131111 A1 | 5/2013 | Coleman et al. |

(Continued)

FOREIGN PATENT DOCUMENTS

WO    WO-2020132045 A1 *    6/2020    ........... A61K 31/416

OTHER PUBLICATIONS

Tan et al., Neuroprotective effects of FK866 against traumatic brain injury: Involvement of p38/ERK pathway, Annals of Clinical and Translational Neurology, vol. 7, No. 5, 742-756, 2020 (Year: 2020).*

(Continued)

*Primary Examiner* — Sarah Pihonak
*Assistant Examiner* — Padmaja S Rao
(74) *Attorney, Agent, or Firm* — Casimir Jones, S.C.; Kelly A. Barton

(57) ABSTRACT

Provided herein are methods for inhibiting or preventing neuron injury or death. The methods comprise contacting one or more neurons with small molecule modulators of one or more mitogen-activated kinase kinase kinases (MAP3Ks), a nicotinamide phosphoribosyltransferase (NAMPT), or a combination thereof.

18 Claims, 26 Drawing Sheets
(12 of 26 Drawing Sheet(s) Filed in Color)

(51) Int. Cl.
  A61K 31/4409  (2006.01)
  A61K 31/4439  (2006.01)
  A61K 31/4545  (2006.01)
  A61K 31/506   (2006.01)
  A61K 31/706   (2006.01)
  A61K 45/06    (2006.01)
  A61P 25/02    (2006.01)
  A61P 25/28    (2006.01)

(52) U.S. Cl.
  CPC ...... *A61K 31/4439* (2013.01); *A61K 31/4545* (2013.01); *A61K 31/506* (2013.01); *A61K 31/706* (2013.01); *A61K 45/06* (2013.01); *A61P 25/02* (2018.01); *A61P 25/28* (2018.01)

(56) References Cited

U.S. PATENT DOCUMENTS

2014/0079712 A1  3/2014  Freeman et al.
2017/0137441 A1  5/2017  Bair et al.

OTHER PUBLICATIONS

Adams & Murray, Atlas of post-mortem techniques in neuropathology, vol. 1982. Cambridge: Cambridge University Press; 1982.
Arevalo et al., "The neuroprotective actions of oestradiol and estrogen receptors" Nat Rev Neurosci. Jan. 2015; 16(1):17-29.
Blumbergs et al., "Diffuse axonal injury in head trauma." J Neurol Neurosurg Psychiatry. Jul. 1989; 52(7): 838-841.
Blumbergs et al., "Staining of amyloid precursor protein to study axonal damage in mild head injury" Lancet. Oct. 15, 1994; 344(8929):1055-6.
Bricker-Anthony et al., "Neurodegeneration and Vision Loss after Mild Blunt Trauma in the C57Bl/6 and DBA/2J Mouse" PLoS One. Jul. 6, 2015; 10(7):e0131921.
Fernandes et al., "DLK-dependent signaling is important for somal but not axonal degeneration of retinal ganglion cells following axonal injury" Neurobiol Dis. Sep. 2014; 69: 108-116.
Foda & Marmarou, "A new model of diffuse brain injury in rats. Part II: Morphological characterization" J Neurosurg. Feb. 1994; 80(2):301-13.
Centers for Disease Control and Prevention. (2015). Report to Congress on Traumatic Brain Injury in the United States: Epidemiology and Rehabilitation. National Center for Injury Prevention and Control; Division of Unintentional Injury Prevention. Atlanta, GA.
Ghosh et al., "DLK induces developmental neuronal degeneration via selective regulation of proapoptotic JNK activity" J Cell Biol. Sep. 5, 2011; 194(5):751-64.
Gilley & Coleman, "Endogenous Nmnat2 Is an Essential Survival Factor for Maintenance of Healthy Axons" PLoS Biol. 2010; 8(1):e1000300.
Green & Simpkins, "Neuroprotective effects of estrogens: potential mechanisms of action" Int J Dev Neurosci. Jul.-Aug. 2000; 18(4-5):347-58.
Holland et al., "Palmitoylation controls DLK localization, interactions and activity to ensure effective axonal injury signaling" Proc Natl Acad Sci USA. Jan. 19, 2016;113(3):763-8.
Jakobs et al., "Retinal ganglion cell degeneration is topological but not cell type specific in DBA/2J mice" J Cell Biol. Oct. 24, 2005; 171(2):313-25.
Karaman et al., "A quantitative analysis of kinase inhibitor selectivity" Nature Biotechnology 2008, 26: 127-132.
Koliatsos et al., "A mouse model of blast injury to brain: initial pathological, neuropathological, and behavioral characterization" J Neuropathol Exp Neurol. May 2011;70(5):399-416.
Lekovitch-Verbin, "Animal models of optic nerve diseases" Eye 2004, 18: 1066-1074.
Libby et al., "Susceptibility to neurodegeneration in a glaucoma is modified by Bax gene dosage" PLoS Genet. Jul. 2005; 1(1):17-26.
Lim et al., "Neural activity promotes long-distance, target-specific regeneration of adult retinal axons" Nature Neuroscience 2016, 19:1073-1084.
Lobato, "Historical vignette of Cajal's work "Degeneration and regeneration of the nervous system" with a reflection of the author" Neurocirugia (Astur). Oct. 2008; 19(5):456-68.
Marmarou et al., "A new model of diffuse brain injury in rats. Part I: Pathophysiology and biomechanics" J Neurosurg. Feb. 1994; 80(2):291-300.
Miller et al., "A dual leucine kinase-dependent axon self-destruction program promotes Wallerian degeneration" Nat Neurosci. Apr. 2009; 12(4):387-9.
Mittl et al., "Prevalence of MR evidence of diffuse axonal injury in patients with mild head injury and normal head CT findings" AJNR Am J Neuroradiol. Sep. 1994; 15(8):1583-9.
Mollayeva et al., "Traumatic brain injury: sex, gender and intersecting vulnerabilities" Nat Rev Neurol. Dec. 2018; 14(12):711-722.
Povlivshock et al., "Impact acceleration injury in the rat: evidence for focal axolemmal change and related neurofilament sidearm alteration" J Neuropathol Exp Neurol. Apr. 1997; 56(4):347-59.
Raghava et al., "Neuroprotective effects of estrogen in CNS injuries: insights from animal models" Neurosci Neuroecon. 2017; 6:15-29.
Shen et al., "Systematic Review of Traumatic Brain Injury and the Impact of Antioxidant Therapy on Clinical Outcomes" Worldviews Evid Based Nurs. Oct. 2016; 13(5):380-389.
Shin et al., "SCG10 is a JNK target in the axonal degeneration pathway" PNAS 2012, 109(52): E3696-E3705.
Strich, "Diffuse degeneration of the cerebral white matter in severe dementia following head injury" J Neurol Neurosurg Psychiatry. Aug. 1956; 19(3):163-85.
Summers et al., "Palmitoylation enables MAPK-dependent proteostasis of axon survival factors" Proc Natl Acad Sci U S A. Sep. 11, 2018; 115(37):E8746-E8754.
Tang et al., "Brain accumulation of sunitinib is restricted by P-glycoprotein (ABCB1) and breast cancer resistance protein (ABCG2) and can be enhanced by oral elacridar and sunitinib coadministration" Int J Cancer. Jan. 1, 2012; 130(1):223-33.
Villegas-Perez et al., "Rapid and protracted phases of retinal ganglion cell loss follow axotomy in the optic nerve of adult rats" J Neurobiol. Jan. 1993; 24(1):23-36.
Wang et al., "Traumatic Axonal Injury in the Optic Nerve: Evidence for Axonal Swelling, Disconnection, Dieback, and Reorganization" J Neurotrauma. Jul. 2011; 28(7): 1185-1198.
Watkins et al., "DLK initiates a transcriptional program that couples apoptotic and regenerative responses to axonal injury" PNAS, Mar. 5, 2023, 110(10): 4039-4044.
Welsbie et al., "Enhanced Functional Genomic Screening Identifies Novel Mediators of Dual Leucine Zipper Kinase-Dependent Injury Signaling in Neurons" Neuron. Jun. 21, 2017; 94(6):1142-1154.e6.
Welsbie et al., "Functional genomic screening identifies dual leucine zipper kinase as a key mediator of retinal ganglion cell death" Proc Natl Acad Sci U S A. Mar. 5, 2013; 110(10):4045-50.
Whitmore et al., "Glaucoma: thinking in new ways-a rôle for autonomous axonal self-destruction and other compartmentalised processes?" Prog Retin Eye Res. Nov. 2005; 24(6):639-62.
Xiong et al., "Protein turnover of the Wallenda/DLK kinase regulates a retrograde response to axonal injury" J Cell Biol. Oct. 4, 2010; 191(1):211-23.
Xu et al., "Repetitive mild traumatic brain injury with impact acceleration in the mouse: Multifocal axonopathy, neuroinflammation, and neurodegeneration in the visual system" Experimental Neurology, Jan. 2016, 275: 436-449.
Yang et al., "Pathological axonal death through a MAPK cascade that triggers a local energy deficit" Cell. Jan. 15, 2015; 160(1-2):161-76.
Ziogas & Koliatsos, "Primary Traumatic Axonopathy in Mice Subjected to Impact Acceleration: A Reappraisal of Pathology and Mechanisms with High-Resolution Anatomical Methods" J Neurosci. Apr. 18, 2018;38(16):4031-4047.

(56) References Cited

OTHER PUBLICATIONS

Bruzzone S., et al., "Catastrophic NAD+ Depletion in Activated T Lymphocytes Through Nampt Inhibition Reduces Demyelination and Disability in EAE," PLOS One, Nov. 19, 2009, vol. 4, No. 11 (e7897), pp. 1-14.
Buki A., et al., "All Roads Lead to Disconnection?—Traumatic Axonal Injury Revisited", Acta Neurochir (Wien), Feb. 2006, vol. 148, No. 2, pp. 181-194.
Busso N., et al., "Pharmacological Inhibition of Nicotinamide Phosphoribosyltransferase/Visfatin Enzymatic Activity Identifies a New Inflammatory Pathway Linked to NAD," PLoS One, May 21, 2008, vol. 3, No. 5 (e2267), 10 Pages.
Capurso S.A., et al., "Deafferentation Causes Apoptosis in Cortical Sensory Neurons in the Adult Rat," The Journal of Neuroscience, Oct. 1, 1997, vol. 17, No. 19, pp. 7372-7384.
Chung K., et al., "Structural and Molecular Interrogation of Intact Biological Systems," Nature, May 16, 2013, vol. 497, No. 7449, pp. 332-337, (8 Pages).
Clatterbuck R E., et al., "Peripheral Nerve Grafts Exert Trophic and Tropic Effects on Anterior Thalamic Neurons," Neurobiology of Disease, 1998, vol. 5, pp. 17-26.
Conforti L., et al., "Wallerian Degeneration: An Emerging Axon Death Pathway Linking Injury and Disease," Nature Reviews Neuroscience, Jun. 2014, vol. 15, No. 6, pp. 394-409.
Essuman K., et al., "The SARM1 Toll/Interleukin-1 Receptor (TIR) Domain Possesses Intrinsic NAD+ Cleavage Activity That Promotes Pathological Axonal Degeneration," Neuron, Mar. 22, 2017, vol. 93, No. 6, pp. 1334-1343.e5, (25 Pages).
Fuchs Y., et al., "Programmed Cell Death in Animal Development and Disease," Cell, Nov. 11, 2011, vol. 147, No. 4, pp. 742-758, 36 Pages.
Gerdts J., et al., "SARM1 Activation Triggers Axon Degeneration Locally via NAD+ Destruction," Science, Apr. 24, 2015, vol. 348, No. 6233, pp. 453-457 (14 Pages).
Gerdts J., et al., "Axon Self-Destruction: New Links Among SARM1, Mapks, and NAD+ Metabolism," Neuron, Feb. 3, 2016, vol. 89, No. 3, pp. 449-460 (26 Pages).
Greer J.E., et al., "Diffuse Traumatic Axonal Injury in the Mouse Induces Atrophy, c-Jun Activation, and Axonal Outgrowth in the Axotomized Neuronal Population," Journal of Neuroscience, Mar. 30, 2011, vol. 31, No. 13, pp. 5089-5105.
Greer J.E., et al., "Mild Traumatic Brain Injury in the Mouse Induces Axotomy Primarily within the Axon Initial Segment," Acta Neuropathologica, Jul. 2013, vol. 126, No. 1, pp. 59-74.
Hanell A., et al., "Traumatic Brain Injury-induced Axonal Phenotypes React Differently to Treatment," Acta Neuropathologica, Feb. 2015, vol. 129, No. 2, pp. 317-332.
Haynes S.E., et al., "The P2Y12 Receptor Regulates Microglial Activation by Extracellular Nucleotides," Nature Neuroscience, Dec. 2006, vol. 9, No. 12, pp. 1512-1519.
Hill C.S., et al., "Traumatic Axonal Injury: Mechanisms and Translational Opportunities," Trends in Neurosciences, May 2016, vol. 39, No. 5, pp. 311-324.
Hosmane S., et al., "Circular Compartmentalized Microfluidic Platform: Study of Axon-glia Interactions," Lab on a Chip, Mar. 21, 2010, vol. 10, No. 6, pp. 741-747.
Howitz K.T, et al., "Small Molecule Activators of Sirtuins Extend Saccharomyces Cerevisiae Lifespan," Nature, Sep. 11, 2003, vol. 425, No. 6954, pp. 191-196.
Kim Y., et al., "MyD88-5 Links Mitochondria, Microtubules, and JNK3 in Neurons and Regulates Neuronal Survival," Journal of Experimental Medicine, Sep. 3, 2007, vol. 204, No. 9, pp. 2063-2074.
Kobayashi K., et al., "P2Y12 Receptor Upregulation in Activated Microglia is a Gateway of P38 Signaling and Neuropathic Pain," The Journal of Neuroscience, Mar. 12, 2008, vol. 28, No. 11, pp. 2892-2902.
Liu H-W., et al., "Pharmacological Bypass of Nad+ Salvage Pathway Protects Neurons From Chemotherapy-induced Degeneration," The Proceedings of the National Academy of Sciences, USA, Oct. 16, 2018, vol. 115, No. 42, pp. 10654-10659, XP055742299, (Published Online on Sep. 26, 2018).
Maxwell W.L., et al., "Ultrastructural Evidence of Axonal Shearing as a Result of Lateral Acceleration of the Head in Non-human Primates," Acta Neuropathologica, 1993, vol. 86, No. 2, pp. 136-144.
Nahimana A., et al., "The NAD Biosynthesis Inhibitor APO866 has Potent Antitumor Activity Against Hematologic Malignancies," Blood, Apr. 2, 2009, vol. 113, No. 14, pp. 3276-3286, (Prepublished Online on Feb. 5, 2009).
Osterloh J.M., et al., "dSarm/Sarm1 Is Required for Activation of an Injury-Induced Axon Death Pathway," Science, Jul. 27, 2012, vol. 337, No. 6093, pp. 481-484 (11 Pages).
Paxinos G., et al., "Paxinos and Franklin's the Mouse Brain in Stereotaxic Coordinates," The Netherlands: Elsevier, Amsterdam, 2012, 3 Pages, TOC only.
Porrero C., et al., "Mapping of Fluorescent Protein-Expressing Neurons and Axon Pathways in Adult and Developing Thy1-eYFP-H Transgenic Mice," Brain Research, Jul. 23, 2010, vol. 1345, pp. 59-72.
Povlishock J.T., et al., "Axonal Response to Traumatic Brain Injury: Reactive Axonal Change, Deafferentation, and Neuroplasticity", Journal of Neurotrauma, vol. 9, Supplement 1, 1992, pp. S189-S200.
Sasaki Y., et al., "Transgenic Mice Expressing the Nmnat1 Protein Manifest Robust Delay in Axonal Degeneration in Vivo," The Journal of Neuroscience, May 20, 2009, vol. 29, No. 20, pp. 6526-6534.
Smith D.H., et al., "Characterization of Diffuse Axonal Pathology and Selective Hippocampal Damage Following Inertial Brain Trauma in the Pig," The Journal of Neuropathology & Experimental Neurology, Jul. 1997, vol. 56, No. 7, pp. 822-834.
Smith D.H., et al., "Diffuse Axonal Injury in Head Trauma," Journal of Head Trauma Rehabilitation, Jul.-Aug. 2003, vol. 18, No. 4, pp. 307-316.
Stone J.R., et al., "Antibodies to the C-terminus of the (Beta)-amyloid Precursor Protein (APP): a Site Specific Marker for the Detection of Traumatic Axonal Injury," Brain Research, Jul. 21, 2000, vol. 871, No. 2, pp. 288-302.
Summers D.W., et al., "SARM1-Specific Motifs in the TIR Domain Enable NAD(+) Loss and Regulate Injury-Induced SARM1 Activation," Proceedings of the National Academy of Sciences, USA, Oct. 11, 2016, vol. 113, No. 41, pp. E6271-E6280.
Suzuki S., et al., "Mechanisms of Neuroprotection by Estrogen", Endocrine, vol. 29, No. 2, Apr. 2006, pp. 209-215.
Szretter K.J., et al., "The Immune Adaptor Molecule Sarm Modulates Tumor Necrosis Factor Alpha Production and Microglia Activation in the Brainstem and Restricts West Nile Virus Pathogenesis," Journal of Virology, Sep. 2009, vol. 83, No. 18, pp. 9329-9338.
Tomer R., et al., "Advanced CLARITY for Rapid and High-resolution Imaging of Intact Tissues," Nature Protocols, Jul. 2014, No. 9, vol. 7, pp. 1682-1697 (33 Pages).
Van Gool F., et al., "Intracellular NAD levels Regulate Tumor Necrosis Factor Protein Synthesis in a Sirtuin-dependent Manner," Nature Medicine, Feb. 2009, vol. 15, No. 2, pp. 206-210 ( 20 Pages).
Walker L.J., et al., "MAPK Signaling Promotes Axonal Degeneration by Speeding the Turnover of the Axonal Maintenance Factor NMNAT2," Elife, Jan. 17, 2017, vol. 6 (e22540), 20 Pages.
Wang J.T., et al., "Local Axonal Protection by WidS as Revealed by Conditional Regulation of Protein Stability," Proceedings of the National Academy of Sciences of the United States of America, Aug. 18, 2015, vol. 112, No. 33, pp. 10093-10100, (Published Online on Jul. 24, 2015).
Xiong Y., et al., "Animal Models of Traumatic Brain Injury," Nature Reviews Neuroscience, Feb. 2013, vol. 14, No. 2, pp. 128-142 (32 Pages), (Published on Jan. 18, 2013).
Yamada J., et al., "Novel Objective Classification of Reactive Microglia Following Hypoglossal Axotomy Using Hierarchical Cluster Analysis," Journal of Comparative Neurology, Apr. 1, 2013, vol. 521, No. 5, pp. 1184-1201.

(56) References Cited

OTHER PUBLICATIONS

Yuan S., et al., "Amphioxus SARM Involved in Neural Development May Function as a Suppressor of TLR Signaling," The Journal of Immunology, Jun. 15, 2010, vol. 184, No. 12, pp. 6874-6881 (9 Pages).

Ziogas N.K., et al., "Primary Traumatic Axonopathy in Mice Subjected to Impact Acceleration: A Reappraisal of Pathology and Mechanisms with High-Resolution Anatomical Methods," The Journal of Neuroscience, Apr. 18, 2018, vol. 38, No. 16, pp. 4031-4047, (Epub: Mar. 22, 2018), XP055742295.

* cited by examiner

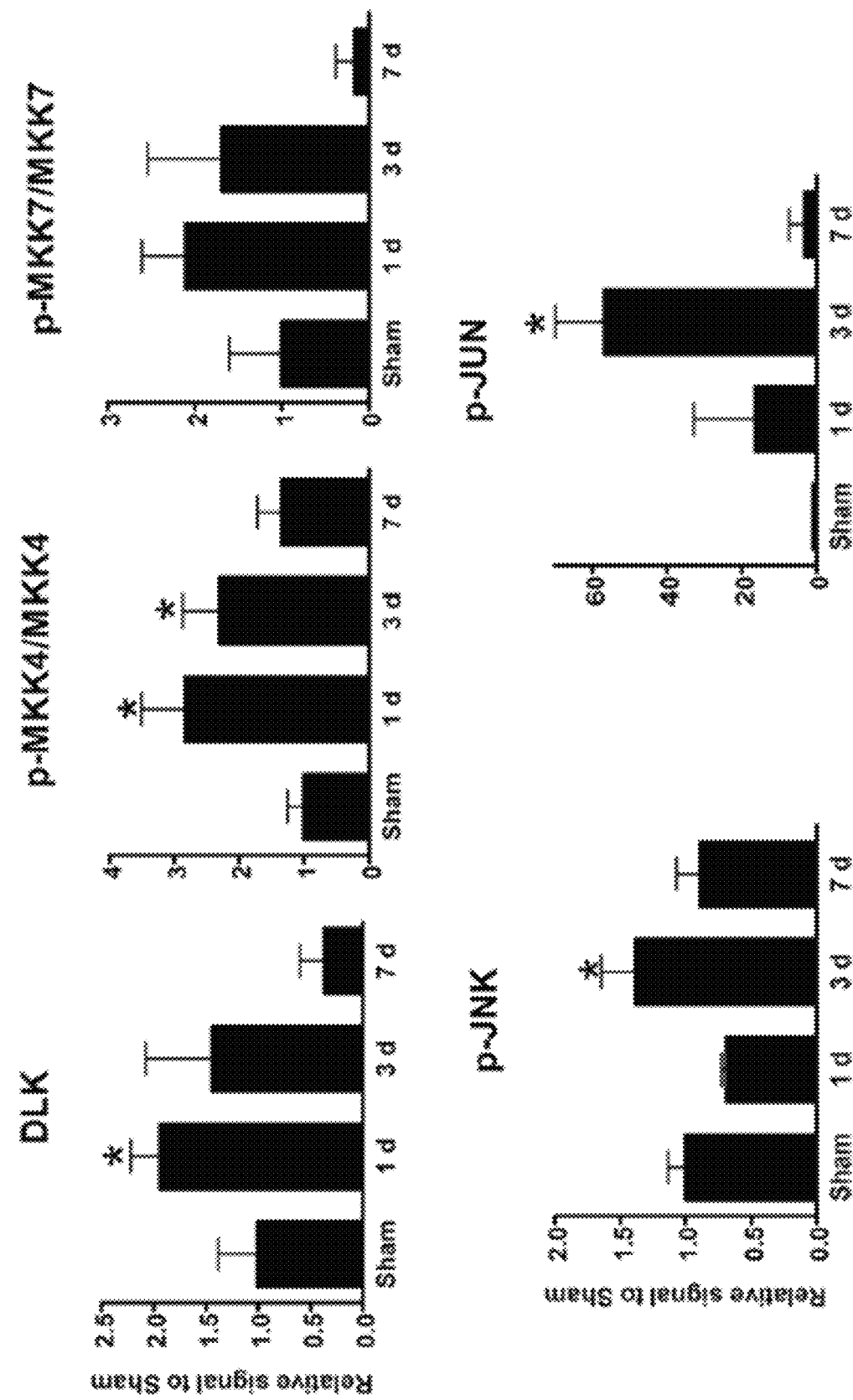
Figure 7, continued

Figure 21

| Experiments/groups | Experimental history; survival time; post-IA | Procedure |
|---|---|---|
| 1. Characterization of initial injury in the optic nerve - general | Sham (n = 3), 4 h post-IA (n = 3), 24 h post-IA (n = 3) IA: 40 g × 1 m or 60 g × 0.85 m | IHC for APP (TAI) and IgG (BBB disruption) |
| 2. Characterization of initial injury in the optic nerve - CLARITY | CTB injection immediately post-IA, survival 2 d post-IA (n = 3) IA: 40 g × 1 m - 60 g × 0.85 m | CLARITY |
| 3. Characterization of traumatic axonopathy - general neuropathology in the optic nerve and tract | 7 d post-IA (n = 3) IA: 40 g × 1 m or 60 g × 0.85 m | Gallyas silver IHC for neuroinflammation (IBA1) |
| 4. Characterization of traumatic axonopathy - death of RGCs in retina | Sham (n = 6), 2 wk post-IA (n = 7), 4 wk post-IA (n = 3) IA: 40 g × 1 m | IHC for γ Synuclein Cell counts on retinal wholemounts |
| 5. Characterization of traumatic axonopathy - axonal degeneration in optic nerve | Sham (n = 6), 2 wk post-IA (n = 7), 4 wk post-IA (n = 3) IA: 40 g × 1 m | Embedding of optic nerve tissues in epoxy resin, semithin sectioning, toluidine blue staining |
| 6. Induction of DLK-JNK pathway in RGCs after injury | 24 h (n = 3), 3 d post-IA (n = 3) IA: 40 g × 1 m | IHC for DLK, p-JUN in retinal sections |
| 7. Time course of DLK-JNK induction in RGCs after injury | Sham (n = 4), 24 h post-IA (n = 10), 3 d post-IA (n = 5), 7 d post-IA (n = 4), 14 d post-IA (n = 3) IA: 40 g × 1 m | IHC for γ Synuclein and p-JUN Cell counts on retinal wholemounts |
| 8. Time course of activation of distinct member of DLK-JNK pathway in RGCs after injury | Sham (n = 3), 24 h post-IA (n = 3), 3 d post-IA (n = 3), 7 d post-IA (n = 3) IA: 40 g × 1 m | Standard Western blotting |
| 9. Interventional studies - genetic deletion of DLK on DLK$^{f/f}$ mice and effects on DLK-JNK pathway activation and RGC survival | AAV2-Cre-GFP into one eye AAV2-GFP into fellow eye (n = 4 each), injections 2 wk pre-IA, euthanasia 3 days post-IA IA: 60 g × 0.85 m | IHC for p-JUN Cell counts on retinal wholemounts |
| | AAV2-Cre-GFP into one eye AAV2-GFP into fellow eye (n = 7 each), injections 2 wk pre-IA, euthanasia 4 wk post-IA IA: 60 g × 0.85 m | IHC for RBPMS Cell counts on retinal wholemounts |
| 10. Interventional studies - genetic deletion of DLK and LZK on DLK$^{f/f}$LZK$^{f/f}$ and effects on DLK-JNK pathway activation and RGC survival | AAV2-Cre-GFP into one eye AAV2-GFP into fellow eye (n = 4 each), injections 2 wk pre-IA, euthanasia 3 day post-IA IA: 60 g × 0.85 m | IHC for p-JUN Cell counts on retinal wholemounts |
| | AAV2-Cre-GFP into one eye AAV2-GFP into fellow eye (n = 7 each), injections 2 wk pre-IA, euthanasia 4 wk post-IA IA: 60 g × 0.85 m | IHC for RBPMS Cell counts on retinal wholemounts |
| 11. Interventional studies - pharmacologic kinase inhibition with sunitinib and effects on DLK-JNK pathway activation and RGC survival | Drug (n = 12) Vehicle (n = 14), both groups 3 wk post-IA IA: 40 g × 1 m | IHC for γ Synuclein Cell counts on retinal wholemounts |

COMBINED MAPK AND NAMPT INHIBITION FOR TREATMENT OF NEURON DEGENERATION

CROSS-REFERENCE TO RELATED APPLICATIONS

This application claims priority to U.S. provisional patent application Ser. No. 63/135,149, filed Jan. 8, 2021, which is incorporated herein by reference in its entirety.

STATEMENT REGARDING FEDERALLY SPONSORED RESEARCH OR DEVELOPMENT

This invention was made with government support under EY028039 awarded by the National Institutes of Health. The government has certain rights in the invention.

FIELD

The disclosure provides methods for inhibiting or preventing neuron injury or death with small molecule modulators of one or more mitogen-activated kinase kinase kinases (MAP3Ks), a nicotinamide phosphoribosyltransferase (NAMPT), or a combination thereof.

BACKGROUND OF THE INVENTION

Neurodegenerative disorders afflict numerous patients throughout the world and can be devastating to patients and caregivers. Such disorders also can result in great financial burdens, with annual costs currently exceeding several hundred billion dollars in the United States alone. Current treatments for such disorders often are inadequate. Further, many such disorders are age-related, and thus their incidence is rapidly increasing as demographics trend toward an aging population. Traumatic brain injury (TBI) is a major cause of central nervous system (CNS) neurodegeneration and has no disease-altering therapies. It is commonly associated with a specific type of biomechanical disruption of the axon called traumatic axonal injury (TAI), which often leads to axonal and sometimes perikaryal degeneration of CNS neurons. Genome-scale, arrayed RNA interference-based screens have been conducted in primary mouse retinal ganglion cells (RGCs) to identify a pair of related kinases, dual leucine zipper kinase (DLK) and leucine zipper kinase (LZK) that are key mediators of cell death in response to simple axotomy. DLK and LZK have been shown to be the major upstream triggers for JUN N-terminal kinase (JNK) signaling following total axonal transection. However, the degree to which DLK/LZK are involved in TAI/TBI is unknown.

BRIEF SUMMARY OF THE INVENTION

The disclosure provides methods for inhibiting or preventing neuron injury or death. In some embodiments, the methods comprise contacting one more neurons with a small molecule that modulates one or more mitogen-activated kinase kinase kinases (MAP3Ks) and/or a small molecule that modulates a nicotinamide phosphoribosyltransferase (NAMPT) in the one or more neurons. In some embodiments, the methods comprise contacting the one or more neurons with an effective amount of a small molecule that modulates one or more mitogen-activated kinase kinase kinases (MAP3Ks) and a small molecule that modulates a nicotinamide phosphoribosyltransferase (NAMPT), and wherein the contacting is simultaneous, sequential, or a combination thereof.

In some embodiments, the one or more MAP3Ks is dual leucine zipper kinase (DLK) and/or leucine zipper kinase (LZK). In some embodiments, the small molecule that modulates one or more MAP3Ks is selected from sunitinib, GNE-3511, CEP-1347, and CEP-11004. In some embodiments, the small molecule that modulates a NAMPT is FK-866.

In some embodiments, the methods comprise contacting one or more neurons with GNE-3511 and FK-866.

In some embodiments, the methods further comprise contacting the one or more neurons with nicotinamide riboside (NaR).

In some embodiments, the one or more neurons are in vivo. In some embodiments, the contacting comprises administering the small molecule that modulates one or more mitogen-activated kinase kinase kinases (MAP3Ks) and/or the small molecule that modulates a nicotinamide phosphoribosyltransferase (NAMPT) to a subject.

In some embodiments, the subject is a human. In some embodiments, the subject has experienced a traumatic brain injury.

In some embodiments, the inhibiting or preventing neuron injury or death comprises suppression of axon fragmentation, suppression of the loss of axonoprotective proteins, modulation of the metabolic profile of the one or more neurons, reduction of axonal degradation and/or synaptic degradation, or a combination thereof.

The disclosure further provides methods for treating or preventing a neuropathy or axonopathy in a subject in need thereof. In some embodiments, the methods comprise administering to the subject an effective amount of: a small molecule that modulates one or more mitogen-activated kinase kinase kinases (MAP3Ks); a small molecule that modulates a nicotinamide phosphoribosyltransferase (NAMPT); or a combination thereof. In some embodiments, the subject is human.

In some embodiments, the methods comprise administering to the subject an effective amount of a small molecule that modulates one or more mitogen-activated kinase kinase kinases (MAP3Ks) and a small molecule that modulates a nicotinamide phosphoribosyltransferase (NAMPT), and wherein the administering is simultaneous, sequential, or a combination thereof.

In some embodiments, the methods further comprise administering an effective amount of nicotinamide riboside (NaR).

In some embodiments, the one or more MAP3Ks is dual leucine zipper kinase (DLK) and/or leucine zipper kinase (LZK). In some embodiments, the small molecule that modulates one or more MAP3Ks is selected from sunitinib, GNE-3511, CEP-1347, and CEP-11004. In some embodiments, the small molecule that modulates a NAMPT is FK-866.

In some embodiments, the methods comprise administering to the subject an effective amount of GNE-3511 and FK-866.

In some embodiments, the methods comprise administering an effective amount of nicotinamide riboside (NaR) with FK-866. In some embodiments, the methods comprise administering to the subject an effective amount of GNE-3511, FK-866, and NaR.

In some embodiments, the neuropathy or axonopathy is hereditary or congenital or associated with neurodegenerative disease, motor neuron disease, neoplasia, endocrine disorder, metabolic disease, nutritional deficiency, atherosclerosis, an autoimmune disease, mechanical injury, chemical or drug-induced injury, thermal injury, radiation injury, nerve compression, retinal or optic nerve disorder, mitochondrial dysfunction, progressive dementia demyelinating diseases ischemia and/or stroke infectious disease; or inflammatory disease. In some embodiments, the neuropathy or axonopathy is caused by a traumatic brain injury.

In some embodiments, the onset of treating is within about one to ten hours of injury.

Other aspects and embodiments of the disclosure will be apparent in light of the following detailed description, examples, and accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1C show early axonal and BBB changes with double immunofluorescence for APP (green) and mouse IgG (red). Eyeball is to the left, optic chiasm to the right of panel. Four hours after injury, there are multiple axonal swellings and bulbs (green), evidence of primary TAI at approximately ⅔ of optic nerve from the eyeball. There is also disruption of BBB manifested by IgG leakage (red) in the same area but covering a larger segment of the nerve. There are no APP (+) axonal abnormalities or BBB disruption in the optic nerve of sham mice. Insets show representative lesions in two magnifications at four (FIG. 1B) and 24 (FIG. 1C) hours post-injury. FIG. 1D shows disruption of CTB transport in optic nerve after IA injury: Axonal transport in optic nerve was explored by intravitreally injecting CTB488 1 h after injury. Processed with CLARITY 2 days after injury, CTB-488 (green) transport is interrupted at approximately ⅔ of the optic nerve from the eyeball at exactly the same site as APP (+) axonal abnormalities and BBB alterations in FIGS. 1A-1C. FIGS. 1E-1F show details of axonal abnormalities at the level of initial mechanical nerve disruption. Panels are magnifications of identically labeled regions in FIG. 1B, FIG. 1C, and FIG. 1D. Note classical axonal bulbs 4 h post-injury (FIG. 1E), varicosities and undulations at 24 h (FIG. 1F), and the interrupted axonal transport of CTB in most axons in FIG. 1G. Scale bars: FIGS. 1A-1C, 500 μm; FIG. 1D, 550 μm; FIGS. 1E-1G, 50 μm FIGS. 2A-2D are gallyas silver degeneration staining showing axonal pathology (black swellings, lines, trails, dots) 7 days after injury in the optic nerve (ON, FIG. 2A), optic tract (OT, FIG. 2B), and superior colliculus (SC, FIG. 2C). Sham tissues show no silver signal at the same time point (FIG. 2D). FIGS. 2E-2F show neuroinflammatory responses evident by the presence of hypertrophic IBA1 (+) microglia and microglial nodules in these sections prepared 7 days after injury. Note the striking selectivity of neuroinflammation in the visual system (optic nerve [ON] and optic tract [OT]) by comparing IBA1 (+) profiles in ON and OT to normal resting microglia in overlying hypothalamus. Scale bars: FIGS. 2A-2D, 100 μm; FIG. 2E, 80 μm; FIG. 2F, 150 μm FIG. 3D is a bar graph with stereological counts of normal axons in the proximal and distal segments of the optic nerve in the sham condition and at 2 and 4 weeks post injury. Numbers are expressed as percentages of sham because there is a difference in baseline myelinated axons in the proximal and distal segments in this experiment where proximal sections were taken from a plane ~0.5-1 mm posterior to the eye. Scale bars: 100 μm FIG. 5D is a bar graph with densities of surviving SNCG (+) RGCs 2 and 4 weeks post-injury, as compared to sham. Data were analyzed with one-way ANOVA followed by Tukey's post hoc test. * $p<0.05$. Scale bars: FIGS. 5A-5C, 50 μm; inserts in FIGS. 5A and 5C, 100 μm FIGS. 6A, 6C and 6E show horizontal retinal sections processed for DLK immunohistochemistry and demonstrating the induction of DLK immunoreactivity in cell bodies (asterisks) in the ganglion cell layer and in axons in the nerve fiber layer (arrows) 1 and 3 days postinjury. There is very little immunoreactivity in sham retinas (FIG. 6A). FIGS. 6B, 6D and 6F show sections immunostained for p-JUN and the presence of many p-JUN (+) nuclei in the ganglion cell layer 1 and 3 days post-injury. Sham-injured retinas (FIG. 6B) are negative. Scale bars: 50 μm FIGS. 8A-8C show in whole-mount retinas dually stained for the RGC marker γ-synuclein (SNCG) (red) and the DLK-JNK marker p-JUN (green)—there is induction of p-JUN in RGCs at day 1 (FIG. 8B) and attenuation of labeling by day 14 (FIG. 8C). No p-JUN (+) RGCS are seen in the sham scenario (FIG. 8A). Left-sided images have been acquired with green filter combination for red SNCG immunofluorescence, images at the center have been acquired with blue filter combination for green p-JUN immunofluorescence, and panels on the right are merged images in which double-labeled profiles appear orange. Note the extensive colocalization at day 1, based on the large number of orange profiles (FIG. 8B, right panel). Most p-JUN (+) nuclei at day 14 seem to belong to smaller or atrophic RGCs (FIG. 8C). FIGS. 8D-8E are bar graphs of densities of p-JUN (+) RGCs in the retinas of sham and injured animals at 1, 3, 7, and 14 days post-injury (FIG. 8D), and of the ratios of densities of p-JUN (+) RGCs over densities of total RGCs from two representative time points, 1 and 14 days (FIG. 8E). Significant differences are indicated with asterisks. The comparison in FIG. 8E was done to ensure that reduction in numbers of double labeled profiles in FIG. 9D was not simply an artifact of the progressive death of RGCs. Data were analyzed with one-way ANOVA followed by Tukey's post hoc test for FIG. 8D and with student's t-test for FIG. 8E. * $p<0.05$. Scale bars: 25 µm FIGS. 9A-9D are representative images of p-JUN (FIGS. 9A and 9C) and RBPMS (FIGS. 9B and 9D) immunostained retinas in which Dlk and Lzk was deleted (AAV-Cre-GFP, FIGS. 9C-9D) and retinas from fellow eyes in which Dlk and Lzk were left intact (AAV-GFP, FIGS. 9A-9B). Images illustrate the suppression of p-JUN immunoreactivity at day 3 postinjury (FIG. 9C) and improved RGC survival 30 days post-injury (FIG. 9H) with combined Dlk/Lzk deletion. FIGS. 9E-9H are bar graphs with quantitative assessments of the effects of Dlk or Dlk/Lzk deletion on p-JUN expression measured at day 3 after injury (FIGS. 9E and 9F, respectively) and also the effects of Dlk or Dlk/Lzk deletion on RGC survival measured 30 days after injury (FIGS. 9G and 9H, respectively). Scale bars: FIGS. 9A-9D, 25 µm FIG. 10A is a bar graph showing, DLK-JNK activation in retina was marked by density of p-JUN immunoreactivity in retinal flatmounts that here was measured at day 1 post injury. FIG. 10B is a graph showing survival was based on the density of SNCG (+) cells that was measured 3 weeks post injury. Data were analyzed with one-way ANOVA followed by Tukey's post hoc test. * $p<0.05$, $p<0.01$, *$p<0.001$ FIGS. 11A and 11B are representative images from semithin sections of the proximal optic nerve 3 days post injury showing the protective effect of Dlk/Lzk deletion. Cre-treated optic nerve is depicted on the right (FIG. 11B) and control optic nerve from the fellow eye is shown on the left (FIG. 11A). FIGS. 11C-11J are bar graphs with counts of axons in the optic nerve proximal (FIGS. 11C-11D and 11G-11H) and distal (FIGS. 11E-11F and 11I-11J) to the site of the initial traumatic disruption three (FIGS. 11D-11F) and 30 (FIGS. 11G-11J) days post injury in Dlkfl/fl (FIGS. 11C, 11E, 11G, and 11I) or Dlkfl/flLzkfl/fl (FIGS. 11D, 11F, 11H, 11J) mice treated with Cre or control (GFP) vectors in the two eyes. There are eight combinations of genotype×proximal or distal location×early or late time point post injury. Of all combinations, the only significant effect on axonal degeneration is that of the deletion of both Dlk and Lzk in the proximal nerve early post injury (FIG. 11D). Data were analyzed with student's t-test. * $p<0.05$. Scale bars: FIGS. 11A-11B, 25 µm

FIG. 16A is representative micrographs of transected axons treated at the time of injury with the DLK inhibitor GNE-3511 or vehicle (DMSO) and with the combination of FK866/NaR either at the time of injury or with an 8 h delay. FIG. 16B is a graph of the degeneration index analysis revealing long lasting protection afforded by both early and delayed FK866+NaR treatment which was further augmented by GNE-3511.

FIG. 17A shows relative changes in protein-normalized levels of metabolites in distal axons at 8 hours, following transection and treatment at the time of injury with NAMPT inhibitor FK866 alone or in combination with NaR, or vehicle (DMSO). FIG. 17B shows product/substrate ratios of key enzymatic steps.

FIG. 18A is a western blot of distal axons at 4 and 8 hours after transection and treatment with the DLK inhibitor GNE3511 or vehicle (DMSO). FIG.

18B shows quantification of signal from western blot normalized to actin and with reference to uninjured/untreated axon samples (n=3).

Figure 19A:
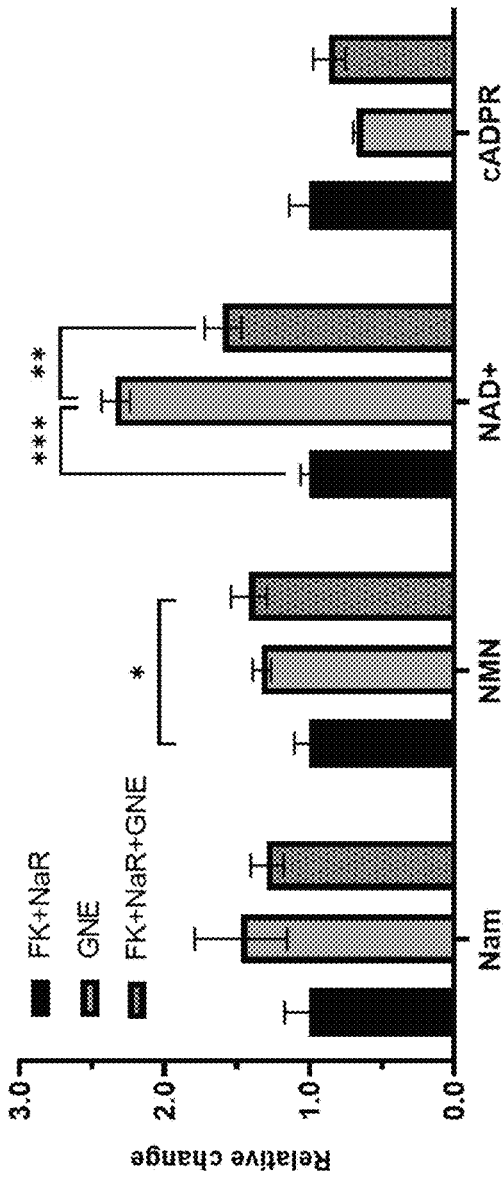
Figure 19B:
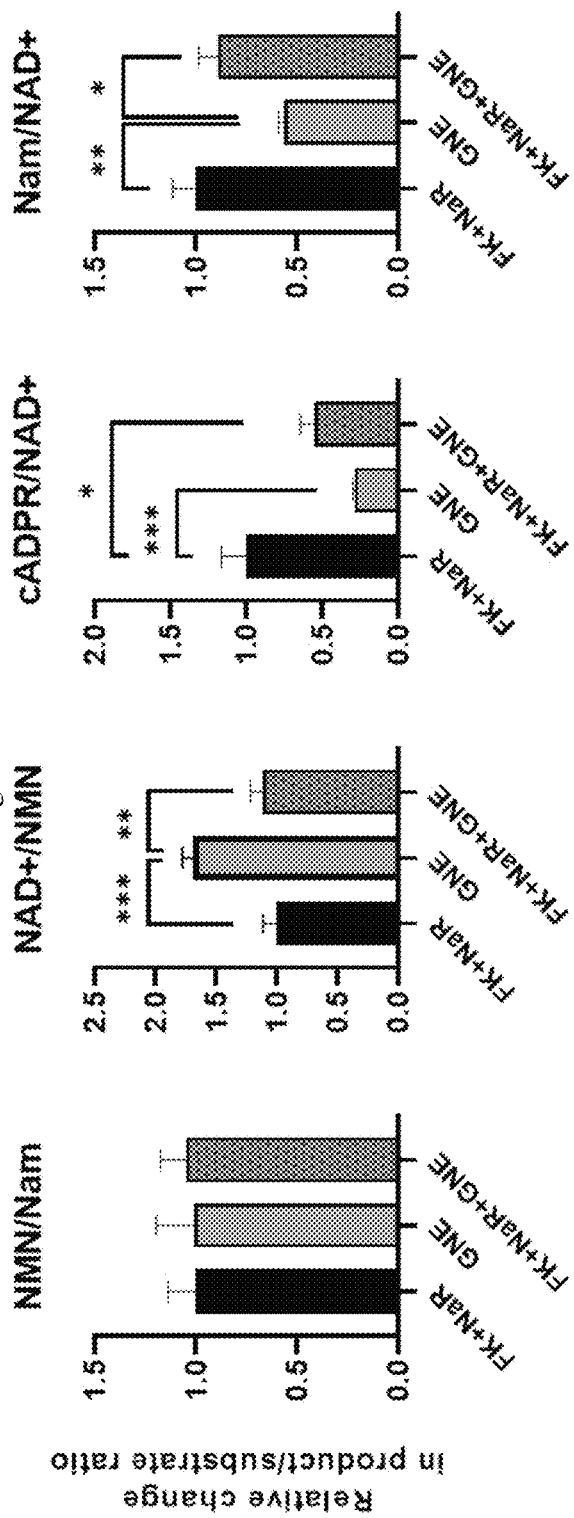

FIGS. 19A and 19B are graphs showing MAPK inhibition alone or in combination with NAMPT inhibition and NaR supplementation favorably modulates the metabolic profile of axotomized axons. FIG. 19A shows the relative changes in protein-normalized levels of metabolites in distal axons at 8 hours, following transection and treatment at the time of injury with the MAPK inhibitor GNE-3511, the NAMPT inhibitor FK866 in combination with NaR, or with the three compounds together. FIG. 19B shows relative changes in product/substrate ratios of key enzymatic steps.

Figure 20:
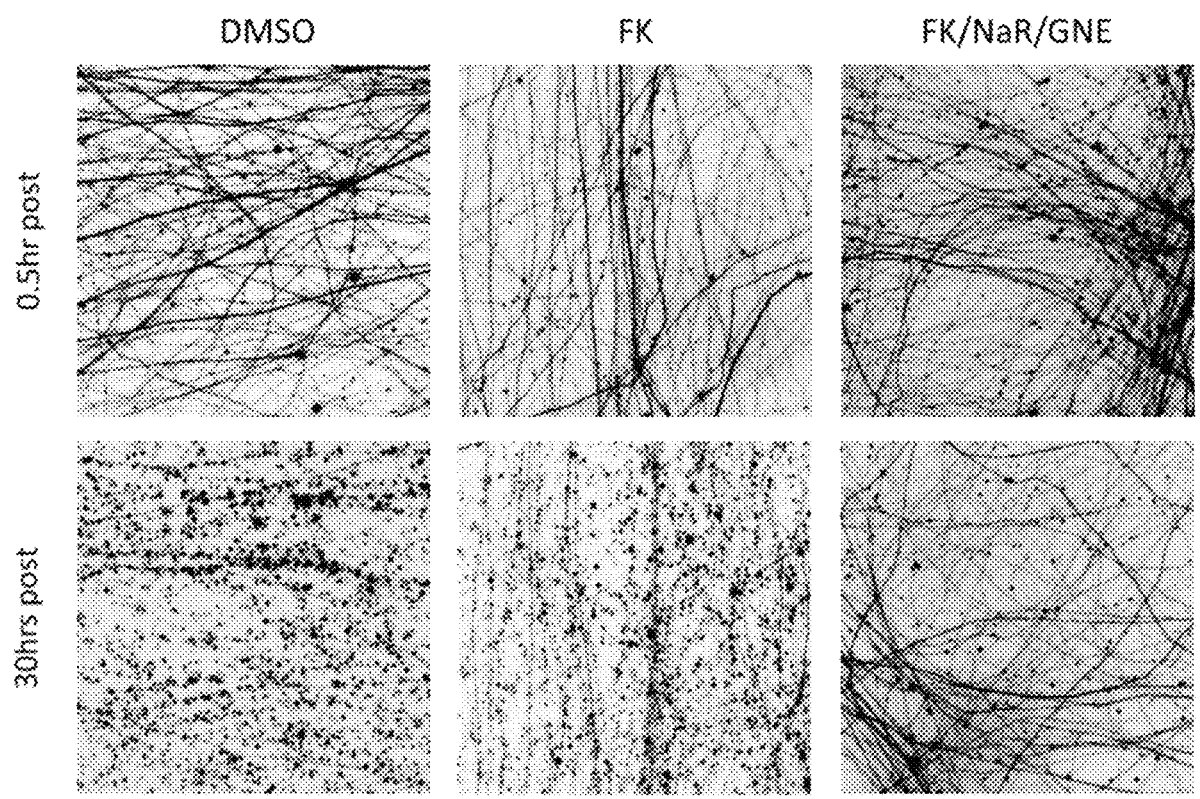

FIG. 20 is images of H9 human embryonic stem cells rapidly differentiated to a cholinergic neuron phenotype using neurogenic mRNA delivery and transduced on DIV 10 neurons with a hSyn-tdTomato containing lentivirus for the fluorescent tracing of axons. On DIV21 axons were transected with a razor blade and treated with vehicle (DMSO), FK866 (FK) or FK866+NaR+GNE3511 (FK/NaR.GNE) and imaged up to 30 h, at indicated time points.

FIG. 21 is a table of the impact acceleration condition and survival time for each experimental group.

DETAILED DESCRIPTION

The present invention involves methods for inhibiting or preventing neuron injury or death. The methods may comprise contacting one more neurons with a small molecule that modulates one or more mitogen-activated kinase kinase kinases (MAP3Ks) and/or a small molecule that modulates a nicotinamide phosphoribosyltransferase (NAMPT) in the one or more neurons. Accordingly, the present invention also involves methods and compositions for treating or preventing a neuropathy or axonopathy and/or diseases or conditions characterized with axonal degradation.

Section headings as used in this section and the entire disclosure herein are merely for organizational purposes and are not intended to be limiting.

1) DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined herein, scientific, and technical terms used in connection with the present disclosure shall have the meanings that are commonly understood by those of ordinary skill in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

The term "contacting" as used herein refers to bring or put in contact, to be in or come into contact. The term "contact" as used herein refers to a state or condition of touching or of immediate or local proximity. Contacting modulators of the disclosed methods to a target destination, such as, a neuron, may occur by any means of administration known to the skilled artisan.

As used herein, the term "modulate" means to change or induce an alteration in a particular biological activity. Modulation includes, but is not limited to, fully or partially stimulating or inhibiting an activity (e.g., by activating a receptor so as to initiate a signal transduction cascade, to inhibit a receptor from propagating a signaling pathway, by activating an endogenous inhibitor that attenuates a biological activity, or by inhibiting the activity of a protein that inhibits a particular biological function). Modulation of a protein that propagates a particular signaling pathway may result in an increase or a decrease in activity, a change in the affinity of one protein in a pathway for another, or another change in the structural, functional, or immunological properties associated with the activity of a pathway or protein within a pathway. In some embodiments herein, the modulate comprises full or partial inhibition of the biological activity.

As used herein, the terms "providing," "administering," "introducing," are used interchangeably herein and refer to the placement into a subject by a method or route which results in at least partial localization to a desired site. The inhibitors, antagonists and agonists of the disclosed methods can be administered by any appropriate route which results in delivery to a desired location in the subject.

As used herein, the term "preventing" refers to partially or indefinitely delaying onset of a disease, disorder and/or condition; partially or completely delaying onset of one or more symptoms, features, or manifestations of a particular disease, disorder, and/or condition; partially or completely delaying progression from a particular disease, disorder and/or condition; and/or decreasing the risk of developing pathology associated with the disease, disorder, and/or condition.

A "subject" or "patient" may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. In one embodiment, the mammal is a human.

As used herein, "treat," "treating" and the like means a slowing, stopping, or reversing of progression of a disease or disorder when provided a compound or composition described herein to an appropriate control subject. The term also means a reversing of the progression of such a disease or disorder to a point of eliminating or greatly reducing the symptoms. As such, "treating" means an application or administration of the compositions described herein to a subject, where the subject has a disease or a symptom of a disease, where the purpose is to cure, heal, alleviate, relieve, alter, remedy, ameliorate, improve, or affect the disease or symptoms of the disease.

2) METHODS FOR INHIBITING OR PREVENTING NEURON INJURY OR DEATH

The disclosure provides methods for inhibiting or preventing neuron injury or death. The methods comprise contacting the one or more neurons with an effective amount of: a small molecule that modulates one or more mitogen-activated kinase kinase kinases (MAP3Ks); a small molecule that modulates a nicotinamide phosphoribosyltransferase (NAMPT); or a combination thereof. In some embodiments, the methods may further comprise contacting the one or more neurons with nicotinamide riboside (NaR).

In some embodiments, the methods comprise contacting the one or more neurons with an effective amount of a small molecule that modulates one or more mitogen-activated kinase kinase kinases (MAP3Ks) and a small molecule that modulates a nicotinamide phosphoribosyltransferase (NAMPT).

In those embodiments in which both MAP3K and NAMPT modulators are used, the contacting with the MAP3K and NAMPT modulators may be simultaneous, sequential, or a combination thereof. For example, the MAP3K and NAMPT modulators may contact the neuron at the same or substantially the same time, or the MAP3K and NAMPT modulators may contact the neuron in succession, in any order, separated by a period of time (e.g., minutes, hours, days, or weeks), or the MAP3K and NAMPT modulators may contact the neuron together at an initial time point and one or both of the MAP3K and NAMPT modulators may contact the neuron at additional time points following the initial time point.

In those embodiments in which the method comprises contacting the one or more neurons with nicotinamide riboside (NaR), contacting the one or more neurons with NaR may be at the same or different times as the MAP3K modulator(s) and/or NAMPT modulator (e.g., may be simultaneous, sequential, or a combination thereof with either or both of the MAP3K modulator(s) and/or NAMPT modulator.

In some embodiments, the one or more neurons are first contacted with the small molecule that modulates one or more MAP3Ks at an initial time point, followed by contact with the small molecule that modulates a NAMPT a period of time after the initial time point (e.g., at 2 hours, 4 hours, 6 hours, 8 hours, or 10 hours post-initial time point). In some embodiments, the one or more neurons are first contacted with the small molecule that modulates one or more MAP3Ks at an initial time point, followed by contact with the small molecule that modulates a NAMPT and NaR a period of time after the initial time point (e.g., at 2 hours, 4 hours, 6 hours, 8 hours, or 10 hours post-initial time point).

In some embodiments, the one or more neurons are in vitro or ex vivo.

In some embodiments, the one or more neurons are in vivo. In some embodiments, the contacting comprises administering the small molecule that modulates one or more MAP3Ks and/or the small molecule that modulates a NAMPT to a subject.

In some embodiments, the subject is a human. In some embodiments, the subject has experienced a traumatic brain injury. Traumatic brain injury (TBI) is associated with mixed neuropathologies, including contusions, diffuse or traumatic axonal injury (TAI), meningeal or parenchymal hemorrhage, and protein aggregation. TAI is the most common pathology regardless of TBI cause or severity and is thought to be the result of dynamic loading of axons during rotational acceleration of the head. This mechanism causes immediate axonal disruption leading to secondary axonal or perikaryal degeneration. One of the distinguishing features of TAI is that injury begins at the axon, as contrasted to axonal damage or degeneration that is secondary to perikaryal injury or cell death.

The inhibition or prevention of neuron injury or death may be mediated by any number of mechanisms. In some embodiments, the inhibition or prevention of neuron injury or death, and as such, the contacting the one or more neurons with a MAP3K modulator and/or a NAMPT modulator, comprises suppression of axon fragmentation. In some embodiments, the inhibition or prevention of neuron injury or death, and as such, the contacting the one or more neurons with a MAP3K modulator and/or a NAMPT modulator, comprises suppression of the loss of axonoprotective proteins. In some embodiments, the inhibition or prevention of neuron injury or death, and as such, the contacting the one or more neurons with a MAP3K modulator and/or a NAMPT modulator, comprises modulation of the metabolic profile of the one or more neurons. In some embodiments, the inhibition or prevention of neuron injury or death, and as such, the contacting the one or more neurons with a MAP3K modulator and/or a NAMPT modulator, comprises reduction of axonal degradation and/or synaptic degradation.

Thus, the disclosure further provides methods for suppressing of axon fragmentation, methods for suppressing the loss of axonoprotective proteins, methods for modulating the metabolic profile of one or more neurons, methods of reducing axonal degradation and/or synaptic degradation, or a combination thereof comprising contacting one or more neurons with a small molecule that modulates one or more MAP3Ks; a small molecule that modulates NAMPT; or a combination thereof. In some embodiments, the methods may further comprise administering to the subject an effective amount of NaR.

3) METHODS FOR TREATING OR PREVENTING A NEUROPATHY OR AXONOPATHY

The disclosure further provides methods for treating or preventing a neuropathy or axonopathy in a subject in need thereof. The methods may comprise administering to the subject an effective amount of: a small molecule that modulates one or more mitogen-activated kinase kinase kinases (MAP3Ks); a small molecule that modulates a nicotinamide phosphoribosyltransferase (NAMPT); or a combination thereof. In some embodiments, the methods may further comprise administering to the subject an effective amount of nicotinamide riboside (NaR). In some embodiments, the subject is a human.

In some embodiments, the methods comprise administering an effective amount of a small molecule that modulates one or more mitogen-activated kinase kinase kinases (MAP3Ks) and a small molecule that modulates a nicotinamide phosphoribosyltransferase (NAMPT).

In those embodiments in which both MAP3K and NAMPT modulators are used, the administration of the MAP3K and NAMPT modulators may be simultaneous, sequential, or a combination thereof. For example, the MAP3K and NAMPT modulators may be administered at the same or substantially the same time, or the MAP3K and NAMPT modulators may be administered in succession, in any order, separated by a period of time (e.g., minutes, hours, days, or weeks), or the MAP3K and NAMPT modulators may be administered together at an initial time point and one or both of the MAP3K and NAMPT modulators may be readministered at additional time points following the initial time point.

In those embodiments, in which nicotinamide riboside (NaR) is also administered to the subject, the administration of NaR may be at the same or different times with the MAP3K modulator(s) and/or NAMPT modulator (e.g., may be simultaneous, sequential, or a combination thereof with either or both of the MAP3K modulator(s) and/or NAMPT modulator. In some embodiments, NaR is administered at the same or substantially the same time as the small molecule that modulates a NAMPT.

In some embodiments, the small molecule that modulates one or more MAP3Ks is administered at an initial time point, followed by sequential administration (e.g., at 2 hours, 4 hours, 6 hours, 8 hours, or 10 hours post-initial time point) of the small molecule that modulates a NAMPT. In some embodiments, the small molecule that modulates one or more MAP3Ks is administered at an initial time point, followed by sequential administration (e.g., at 2 hours, 4 hours, 6 hours, 8 hours, or 10 hours post-initial time point) of the small molecule that modulates a NAMPT and NaR.

In those embodiments, in which both MAP3K and NAMPT modulators are used, the MAP3K and NAMPT modulators may be provided as a single composition. Thus, the present disclosure further provides compositions comprising a MAP3K modulator and a NAMPT modulator. In those embodiments, in which nicotinamide riboside (NaR) is also used, the MAP3K modulator(s) and/or NAMPT modulator may be provided as a single composition with nicotinamide riboside (NaR). In some embodiments, the compositions comprise a NAMPT modulator and nicotinamide riboside (NaR).

Compositions comprising the MAP3K and NAMPT modulators may further comprise excipients or pharmaceutically acceptable carriers. Excipients and carriers may include any and all solvents, dispersion media, antibacterial and antifungal agents, isotonic and absorption delaying agents. Some examples of materials which can serve as excipients and/or carriers are sugars including, but not limited to, lactose, glucose and sucrose; starches including, but not limited to, corn starch and potato starch; cellulose and its derivatives including, but not limited to, sodium carboxymethyl cellulose, ethyl cellulose and cellulose acetate; powdered tragacanth; malt; gelatin; talc; excipients including, but not limited to, cocoa butter and suppository waxes; oils including, but not limited to, peanut oil, cottonseed oil, safflower oil, sesame oil, olive oil, corn oil and soybean oil; glycols; including propylene glycol; esters including, but not limited to, ethyl oleate and ethyl laurate; agar; buffering agents including, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants including, but not limited to, sodium lauryl sulfate and magnesium stearate, as well as coloring agents, releasing agents, preservatives, and antioxidants. Techniques and formulations may be found, for example, in Remington's Pharmaceutical Sciences, 19th Edition (Mack Publishing Company, 1995). The route or administration and the form of the composition usually dictates the type of carrier to be used.

The MAP3K and NAMPT modulators may be administered to a subject by a variety of methods. In any of the uses or methods described herein, administration may be by various routes known to those skilled in the art, including without limitation topical, intraocular, intravenous, intramuscular, subcutaneous, systemic, and/or intraperitoneal administration to a subject in need thereof. In some embodiments, the MAP3K and NAMPT modulators as disclosed herein may be administered by parenteral administration (including, but not limited to, subcutaneous, intramuscular, intravenous, intraperitoneal, intracardiac, intravitreal, and intraarticular injections).

The terms "effective amount" or "therapeutically effective amount," as used herein, refer to a sufficient amount of the MAP3K and NAMPT modulators disclosed herein which will relieve to some extent one or more of the symptoms of the disease or condition being treated or inhibit or prevent neuron injury or death.

The amount of the MAP3K and NAMPT modulators required will vary not only with the particular MAP3K and NAMPT modulators selected but also with the route of administration, the nature and/or symptoms of the disease and the age and condition of the patient and will be ultimately at the discretion of the attendant physician or clinician. The determination of effective dosage levels, that is the dosage levels necessary to achieve the desired result, can be accomplished by one skilled in the art using routine methods, for example, human clinical trials, in vivo studies, and in vitro studies. For example, useful dosages of the MAP3K and NAMPT modulators, can be determined by comparing their in vitro activity, and in vivo activity in animal models.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the symptoms to be treated and the route of administration. Further, the dose, and perhaps dose frequency, will also vary according to the age, body weight, and response of the individual patient. A program comparable to that discussed above may be used in veterinary medicine.

A therapeutically effective amount of the MAP3K and NAMPT modulators, may be administered alone or in combination with a therapeutically effective amount of at least one additional therapeutic agent. In some embodiments, effective combination therapy is achieved with a single composition or pharmacological formulation that includes both agents, or with two distinct compositions or formulations, administered at the same time, wherein one composition includes a MAP3K and/or NAMPT modulator, and the other includes the second agent(s).

Axonal degeneration occurs in the course of traumatic, toxic, metabolic, or ischemic injury and in a variety of neurodegenerative diseases such as Parkinson's, Alzheimer's diseases, and Amyotrophic Lateral Sclerosis. Such diseases and conditions are associated with functional as well as structural demise of axons. The paradigmatic form of axonopathy is Wallerian degeneration, which occurs when the distal portion of the axon is severed from the cell body. The severed axon rapidly succumbs to a strictly regulated, orderly, complete degeneration. Although, in the peripheral nervous system (PNS), the apparent function of such a programmatic axonal breakdown is to clear dysfunctional axons and prepare the ground for regeneration, an ongoing chronic activation of such programs may override the regenerative potential of the nerve. In the central nervous system (CNS), repair/regeneration does not occur or is incomplete. Wallerian degeneration and related processes lead to a loss of large numbers of axons, disconnection among brain regions, brain atrophy, and chronic disability. Because there are no known techniques for intervening to repair axons once degeneration sets in, especially in the CNS, the most effective strategy is to prevent or promptly mitigate Wallerian-type and related axonal breakdown programs in the initiation phase.

Axonal degeneration is a hallmark of peripheral neuropathy, glaucoma, brain injury (e.g., traumatic brain injury), and neurodegenerative disease. Neurodegeneration and neurodegenerative disorders include progressive dysfunction and/or loss of nerve or glial cells in the PNS and CNS. In all these conditions, as explained above, axonopathy is a critical feature of pathology responsible for disease progression, symptoms and signs, and accounts for a large portion of a patient's disability. Thus, also provided herein are methods for reducing axonal degradation in a subject comprising administering to the subject an effective amount of: a small molecule that modulates one or more MAP3Ks; a small molecule that modulates NAMPT; or a combination thereof. In some embodiments, the methods may further comprise administering to the subject an effective amount of NaR.

In some embodiments, the neuropathy or axonopathy is hereditary or congenital or associated with neurodegenerative disease, motor neuron disease, neoplasia, endocrine disorder, metabolic disease, nutritional deficiency, atherosclerosis, an autoimmune disease, mechanical injury, chemical or drug-induced injury, thermal injury, radiation injury, nerve compression, retinal or optic nerve disorder, mitochondrial dysfunction, progressive dementia demyelinating diseases ischemia and/or stroke infectious disease; or inflammatory disease. In select embodiments, the neuropathy or axonopathy is caused by a traumatic brain injury.

The disclosed methods may further comprise selecting a subject with or at risk for developing axonal degradation or a neuropathy or axonopathy. In some embodiments, subjects suitable for treatment can have or be at risk for suffering a traumatic brain injury. In some embodiments, subjects suitable for treatment can have or be at risk of developing neurodegenerative disease. In addition, such subjects can have or be at risk of developing axonal degradation is in the central and/or peripheral nervous system. In some embodiments, a subject with or at risk of developing axonal degradation can have diabetes and/or diabetic neuropathy and/or can undergo chemotherapy and have chemotherapy-induced peripheral neuropathy (e.g., peripheral neuropathy) and/or have glaucoma.

The methods are not limited to a particular time for onset of treatment and/or treatment duration. In some embodiments, the onset of administration or any of all of: the small molecule that modulates one or more MAP3Ks, the small molecule that modulates a NAMPT; or NaR is within approximately one to ten hours of an injury (e.g., 3-5 hours, 2-5 hours, 2-7 hours, 2.5-6.5 hours, 1.5-6.5 hours, 1-7 hours, 2-8 hours, 2.5-8.5 hours, 3-9 hours, etc.). In some embodiments, the methods comprise repeat administration of one or more of the MAP3K modulator, NAPMPT, or NaR. The repeat administration is not limited in duration, but may last for approximately 1-14 days (e.g., 2 days, 3 days, 4 days, 5 days, 7 days, 10 days, 14 days). For example, in some embodiments, the small molecule that modulates one or more MAP3Ks is administered within approximately one to ten hours of an injury and the small molecule that modulates a NAMPT, and optionally NaR, is administered at some time after the initial administration of the small molecule that modulates one or more MAP3Ks (e.g., after 2 hours, 4 hours, 6 hours, 8 hours, or 10 hours).

4) MAP3K AND NAMPT MODULATORS

Mitogen-activated protein kinases (MAP kinases) are functionally connected kinases that regulate key cellular process such as all survival, death, differentiation, and proliferation. The typical MAP kinase module is composed by a cascade of three kinases: a MAP kinase kinase kinase (MAP3K) that phosphorylates and activates a MAP kinase kinase (MAP2K) which phosphorylates a MAP kinase (MAPK). In some embodiments, the one or more MAP3Ks suitable for modulating with the methods disclosed herein comprise a dual leucine zipper kinase (DLK), a leucine zipper kinase (LZK), or a combination thereof.

In some embodiments, the MAP3K modulator(s) acts directly on the target MAP3K. In some embodiments, the MAP3K modulator(s) is a MAP3K inhibitor. Small molecule inhibitors of MAP3Ks include, but are not limited to, GS-4997, 5Z-7-oxozeaenol, URMC-099, CEP-1347, GNE-3511, GNE-8505, NIK SMI1, sunitinib, regorafenib, sorafenib, vemurafenib, dabrafenib, lifirafenib, imatinib, nilotinib, ponatinib, motesanib, encorafenib, and the like. In some embodiments, the small molecule that modulates one or more MAP3Ks is selected from sunitinib, GNE-3511, CEP-1347, and CEP-11004. In some embodiments, the methods comprise use of any type of small molecule compound or pharmaceutical formulation that is capable of inhibiting MAP3K activity and/or expression.

Nicotinamide phosphoribosyltransferase (NAMPT) is a rate-limiting enzyme in the salvage pathway of nicotinamide (NAM) in nicotinamide adenine dinucleotide (NAD$^+$) synthesis. In some embodiments, the NAMPT modulator acts directly on NAMPT. In some embodiments, the NAMPT modulator is a NAMPT inhibitor. In some embodiments, the NAMPT inhibitor is selected from FK866, CHS-828, GPP78, STF118804, and STF31. In some embodiments, the methods comprise use of any type of small molecule compound or pharmaceutical formulation that is capable of inhibiting NAMPT activity and/or expression. In various embodiments, the small molecule that modulates a NAMPT decreases NAMPT activity through inhibiting NAMPT genetic expression.

In some embodiments, the small molecule that modulates one or more MAP3Ks is GNE-3511. In some embodiments, the NAMPT modulator is FK866. In some embodiments, the methods comprise contacting one or more neurons or co-administering GNE-3511 and FK-866.

In some embodiments, the methods comprise administering an effective amount of nicotinamide riboside (NaR) with FK-866. The method may optimize the duration, timing, and robustness of effect of FK866. In some embodiments, the methods comprise administering to the subject an effective amount of GNE-3511, FK-866, and NaR.

Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

5) EXAMPLES

Example 1

This example demonstrates that that the DLK/LZK-JNK axis is involved in retinal ganglion cell (RGC) death associated with traumatic axonal injury (TAI) in the visual system and suggests a broader role of this kinase cascade in primary axonopathies associated with traumatic brain injury (TBI).

Methods

Experimental subjects and IA procedures Eight-week-old male C57BL/6 J wild-type mice and transgenic Dlk$^{fl/fl}$ and Dlk$^{fl/fl}$Lzk$^{fl/fl}$ mice were subjected to IA or sham injury. Male mice were chosen such as to avoid the confounding effects of sex hormones on injury outcomes [25-29]. Wild-type mice and founders were purchased from Charles River Laboratories (Wilmington, MA). Animals were housed in a vivarium with a 12-h light/12-h dark cycle and given ad libitum access to food and water. All animal handling as well as surgical and postoperative procedures were carried out according to protocols approved by the Animal Care and Use Committee of the Johns Hopkins Medical Institutions.

Impact acceleration injury was performed with height weight settings generating kinetic energy of 0.45-0.5 Jupon impact, essentially as described [11, 12] (FIG. 21). Immediately prior to injury, the cranium was exposed and a 5 mm-thick stainless-steel disc was glued onto the skull midway between bregma and lambda sutures. Surgical procedures and injury were performed under aseptic conditions with gas anesthesia (isoflurane:oxygen:nitrous oxide=1:33: 66). Immediately after injury the disc was removed the skull was checked under the surgical microscope for skull fractures. The rare animals with skull fractures were excluded from further study because such events introduce injuries variables that cannot be easily controlled. Sham animals were subjected to the same procedures, but without the weight drop. The scalp incision was closed with surgical staples, and the animal was returned to cage.

Histology, histochemistry, immunohistochemistry and microscopy. At the various survival times listed in FIG. 21, animals were transcardially perfused with freshly depolymerized, 4% neutral-buffered paraformaldehyde. Eyes were enucleated and fixed for 2 h while optic nerves were immersed in the same fixative overnight at 4° C. In some cases, brains were also included in the study for the analysis of optic tracts and superior colliculi. Tissues were cryoprotected in 30% sucrose and stored at −80° C. until further processing. Sagittal brain sections (40 µm), some with attached distal nerves, were prepared in series for Gallyas silver staining for injured/degenerating axons and terminals and immunohistochemistry (IHC) for the microglial marker IBA1. Gallyas silver staining was performed as described [14]. Sagittal retinal sections (10 µm) were prepared on a cryostat and processed in series for immunoperoxidase-based IHC to assay for select members of the DLK-JNK pathway, including DLK, phosphorylated JNK (p-JNK) and phosphorylated JUN (p-JUN). Sagittal sections of the entire optic nerve were used to assay for the presence of axon injury and blood brain barrier (BBB) disruption at early time points post-injury, with amyloid precursor protein (APP) and IgG staining, as described [11]. Retinal flat mounts were prepared as described[11] and used to explore injury responses or survival of RGCs based on p-JUN and γ-synuclein(SNCG) immunofluorescence.

In all experiments involving IHC, sections were first incubated in the primary antibody overnight at 4° C. For immunoperoxidase staining, after incubation with biotinylated secondary antibody (1:200; Jackson ImmunoResearch, West Grove, PA) and then avidin and biotinylated peroxidase, sections were developed with 3,3'-diaminobenzidine (DAB) (Vectastain Elite ABC Kit; Vector Laboratories Inc., Burlingame, CA). For immunofluorescence, after incubation in secondary antibodies conjugated with Cy3 or Cy2 (1:200; Jackson ImmunoResearch, West Grove, PA) for 2-4 h at room temperature, sections were counterstained with the fluorescent DNA dye 4',6-diamidino-2-phenylindole (DAPI) and coverslipped with DPX. Primary antibodies included: anti-IBA1 (1:500; Dako; 019-19,741, Carpinteria, CA or Biocare Medical; CP-290A, Pacheco, CA); DLK (1:200, GeneTex; GTX124127, Irvine, CA); p-JNK (1:200, Cell Signaling Technology; 9251 or 4671, Danvers, MA); p-JUN (1:200, Cell Signaling Technology; 9261 or 3270, Danvers, MA); SNCG (1:600; Abnova; H00006623-M01, Walnut, CA or Genetex; GTX110483, Irvine, CA); RBPMS (1:1000, PhosphoSolutions; 1832-RBPMS or1830-RBPMS, Aurora, CO); and TUJ1 (1:600, Covance; MMS-435P or PRB-435P, Indianapolis, IN or Abcam; ab18207, Cambridge, MA). Immunostained sections were studied on a Zeiss Axiophot microscope equipped for epifluorescence or a Zeiss LSM 510 inverted confocal microscope. Adobe Photoshop 9.0 software (Adobe Systems, San Jose, CA) was used for image processing.

CLARITY-based processing of the optic nerve To explore the location and extent of axonal injury in the optic nerve after IA, the anterograde tracer cholera toxin subunit B (CTB) conjugated with Alexa Fluor® 488 (CTB488) was injected intravitreally 1 h after IA or sham injury. Optic nerves were then dissected and processed by CLARITY as described [12]. In brief, optic nerves were incubated in a hydrogel containing 2% acrylamide, 0.025% bisacrylamide, 0.25% VA-044 initiator and 4% PFA in 0.1 MPBS overnight (4° C.). After degassing, samples were incubated in a water bath (37° C.) for 3 h. Polymerized nerves were then transferred to a boric acid solution with 4% SDS and were incubated for 4 days. Prior to imaging, optic nerves were incubated in FocusClear (CellExplorer catalog #FC-101) and mounted for imaging. Transparent optic nerves were imaged with confocal microscopy at 20× on a Zeiss Axio-Examiner microscope with a 710NLO module (Carl Zeiss Inc., Oberkochen, Germany) and images were visualized with Imaris software (Bitplane, Concord, MA).

Semithin-section processing of the optic nerve Optic nerves from sham- and IA-injured subjects were dissected away from the eyes and brains and treated with a solution containing 4% paraformaldehyde and 0.2% glutaraldehyde for 24 h. After rinsing in 0.1M phosphate buffer (pH 7.3) for 3-10 min, tissues were immersed in 1% osmium tetroxide for 15 min and stained en bloc with 1% uranyl acetate for 1 h. Stained tissues were dehydrated in graded concentrations of ethanol, embedded in Poly/Bed 812 (Polysciences Inc., Warrington, PA) in BEEM® capsules and polymerized at 60° C. for 72 h. Semithin sections (1 µm) were cut transversely from segments of optic nerves caudal to the eyeball and stained with 1% toluidine blue. Myelinated axonal profiles were studied under 100× magnification on a Zeiss Axiophot microscope equipped for epifluorescence (Diagnostic Instruments Inc., Sterling Heights, MI); normal profiles were counted by investigators blinded to experimental history using the optical fractionator probe in the Stereo Investigator® software (Microbrightfield Inc., Williston, VT). Immunoblots To explore the involvement of select members of the DLKJNK axis in visual TAI after IA, fresh eyeballs were harvested at days 1, 3 and 7 after injury and then dissected the retinas and stored them at −80° C. For protein extraction, retinas were sonicated in cell lysis buffer containing 1 mM PMSF (Cell Signaling Technology, Danvers, MA), complete protease inhibitor cocktail and PhosSTOP phosphatase inhibitor cocktail (Roche, Basel, Switzerland) and then incubated for 30 min at room temperature. Solubilized proteins in Laemmli sample buffer were separated on SDS-PAGE gel and then transferred to polyvinylidene fluoride (PVDF) membranes using XCell II blot system (Invitrogen, Carlsbad, CA). Membranes were blocked with 5% Bovine Serum Albumin (BSA) in Tris buffered saline/0.05% Tween-20 and sequentially incubated in primary antibodies (overnight, 4° C.). In addition to DLK, p-JNK and p-JUN (all at 1:1000) antibodies that were the same as in previous section, antibodies were also used against phosphorylated MKK4 and MKK7 (1:1000, Cell Signaling Technology, Danvers, MA), and a β-actin antibody (1:1000, Cell Signaling Technology, Danvers, MA). HRP-conjugated secondary antibody (1 h at RT) and Super Signal Chemiluminescent Substrate (Thermo Scientific. Rockford, IL) was used to detect protein signals. Image J (National Institutes of Health) and Prism (GraphPad Software, Inc., La Jolla, CA) were used for quantitation and statistical analysis. Dlk/Lzk knockout in $Dlk^{fl/fl}$ and $Dlk^{fl/fl}Lzk^{fl/fl}$ mice Male $Dlk^{fl/fl}$ and $Dlk^{fl/fl}Lzk^{fl/fl}$ mice were subjected to IA as described above [11, 12]. Two weeks prior to injury, subjects were intravitreally injected in one eye with AAV2 expressing Cre-GFP (AAV-Cre) and in the fellow eye with AAV2 expressing GFP (AAVGFP). In one set of experiments (n=5 per Dlkfl/fl, Dlkfl/fl Lzkfl/f and wild-type mice), 3 days after injury, retinal flat mounts were immunostained for p-JUN and taken for counts of immunoreactive neurons as laid out in previous sections, with the AAV2-GFP injected eye serving as control. In another experimental scenario (n=9-10 per Dlkfl/fl, Dlkfl/fl Lzkfl/fl and wild-type mice) animals were allowed to survive for 3 weeks and retinal flat mounts were processed for counts of SNCG-positive or RBPMS-positive RGCs as described in previous Sections. DLK-JNK inhibition with the protein kinase inhibitor sunitinib stock solution was made by dissolving drug powder in dimethylsulfoxide (DMSO) at a concentration of 120 mg/ml and was stored at −20° C. At the time of drug administration, stock solution was diluted with saline to a final concentration of 6 mg/ml and injected intraperitoneally into mice (60 mg/kg). Sunitinib was administered 24 and 4 h prior to injury, and then once more immediately after the injury (for the evaluation of p-JUN expression in RGCs) or daily for 3 weeks starting immediately after the injury (for the evaluation of RGC survival). Control animals received injections of vehicle solution. RGC counts in retinal flat mounts. The four quadrants of retinal mounts immunolabeled with SNCG and p-JUN were separately imaged with a 20× objective (0.4 numerical aperture) on a Zeiss LSM 510 inverted confocal microscope (Carl Zeiss Inc., Oberkochen, Germany). Images were adjusted for optimal contrast and brightness with Adobe Photoshop 7.0 and Image J was used to count surviving SNCG (+), RBPMS (+) or injured p-JUN (+) RGCs. Cells were counted in 150×150 μm fields from three concentric zones of the same width, from the center to the periphery of the retina, using at least 8 fields per each zone. Cell density was calculated by dividing cell numbers by total area surveyed. The ratio of p-JUN (+) RGCs cells was calculated by dividing the number of p-JUN/SNCG double-labeled cells by the total number of SNCG (+) cells. In a number of experiments, e.g., p-JUN response and survival of RGCs in $DIV^{fl/fl}$ and $Dlk^{fl/fl}Lzk^{fl/fl}$ mice and RGC survival in the sunitinib experiment, counts were done using an automated image analysis system (ImageXpress high content imager, Molecular Devices, Sunnyvale CA) using the autofocus and auto-tiling function at 20× magnification followed by automatic quantification with ImageJ. Statistical methodologies Statistical analysis was carried out with one-way ANOVA or t test. In the case of ANOVA, significant differences were further analyzed with Tukey's post hoc test to reveal important main effects or interactions. For counts of axonal number in the characterization of optic neuropathy, numbers were normalized to sham mean. Calculations were performed using Prism 4 (GraphPad Software). Differences were considered significant at $p<0.05$.

Results

Figures 1A, 1B, 1C, 1D, 1E, 1F, 1G:
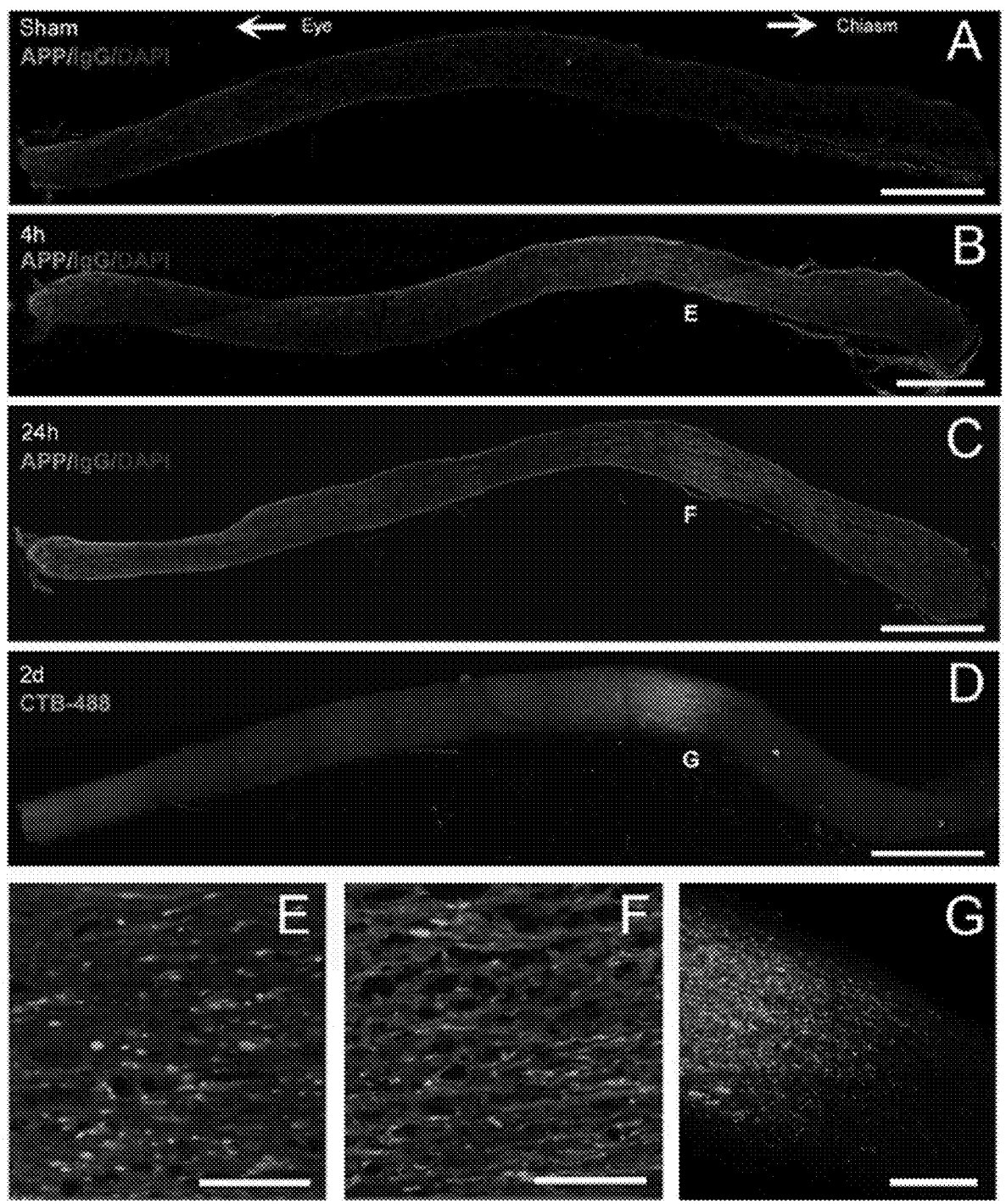
FIGS. 1A-1G are images showing the location of the initial optic nerve disruption injury in IA-injured animals.
Figures 2A, 2B, 2C, 2D, 2E, 2F:
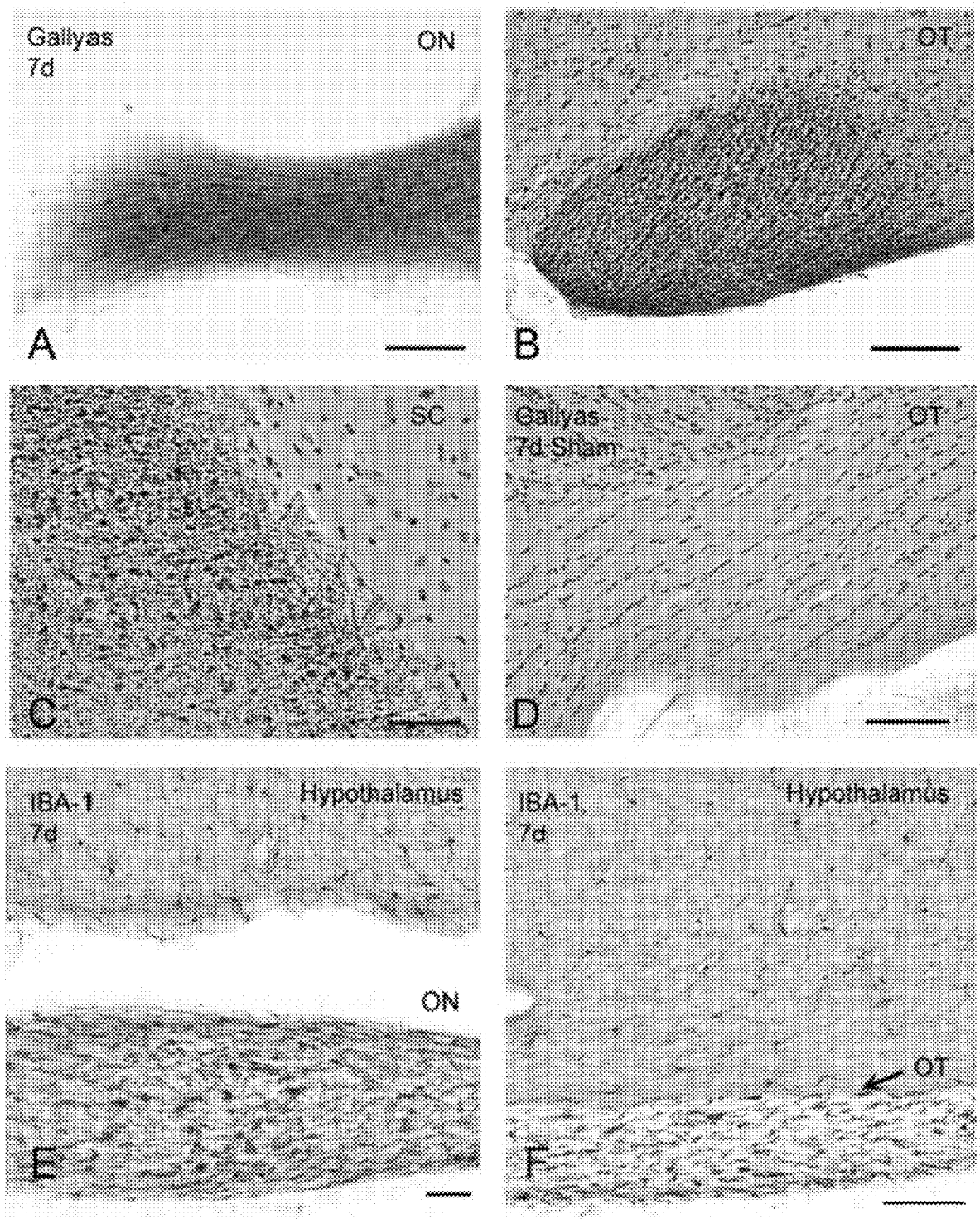
FIGS. 2A-2F are images showing axonal degeneration (Gallyas silver) and neuroinflammation in the visual system after IA injury.
Figures 3A, 3B, 3C, 3D:
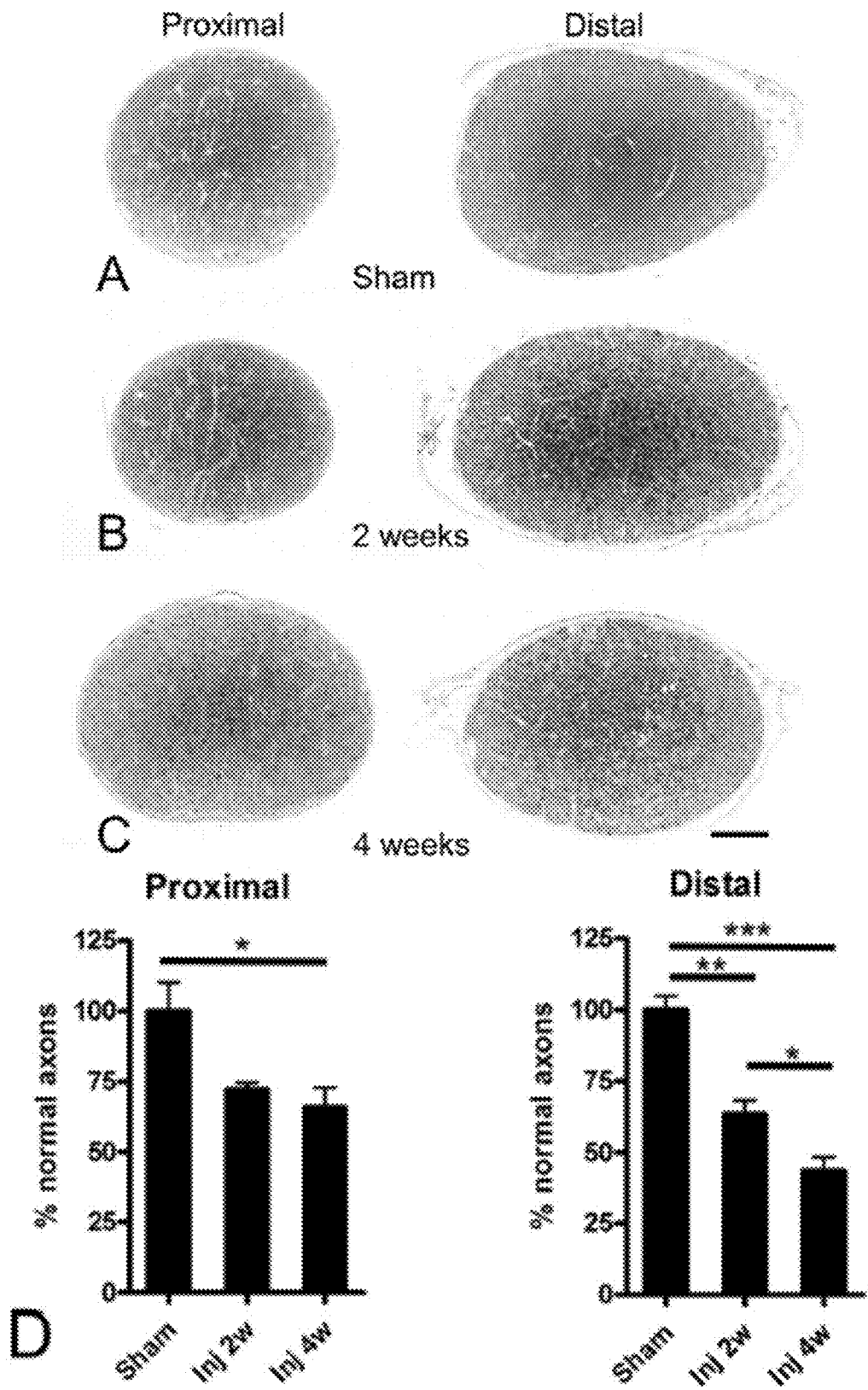
FIGS. 3A-3D show axonal degeneration in the proximal and distal optic nerve following IA injury. Axonal pathology in the optic nerve of mice was examined with toluidine blue staining of semithin sections from sham (FIG. 3A) and 2- or 4-week post-injury cases (FIGS. 3B and 3C, respectively). The nerve segment proximal to initial traumatic disruption is on the left, distal to disruption segment (close to chiasm) is on the right. Within the first month, there is evident axonopathy, distal more than proximal. In both segments and time points, pathology is more severe at the center of the nerve. Fields are further enlarged for greater cellular detail in FIG. 4.
Figures 4A, 4B, 4C:
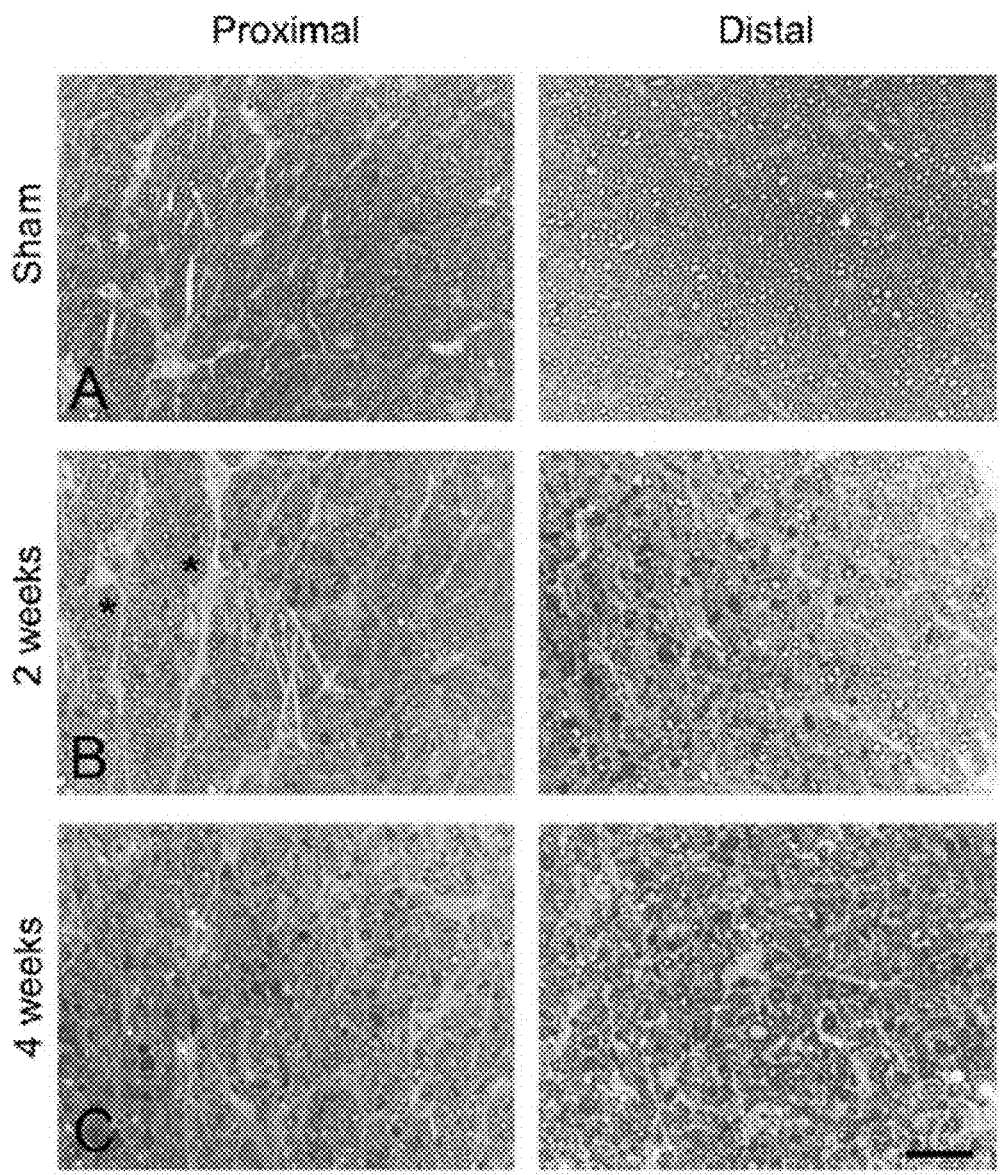
FIGS. 4A-4C are images showing the details of traumatic axonopathy in the optic nerve at the semithin level. Illustrated fields are from the same sections used for FIG. 3. All panels are from toluidine blue-stained semithin sections of the optic nerve proximal to the initial traumatic disruption of the nerve (close to the eye; left panels) and distal to traumatic disruption (towards the optic chiasm; right panels). The sham condition is illustrated in (FIG. 4A), and representative fields from lesioned nerves two and 4 weeks post injury are illustrated in FIGS. 4B and 4C. The main finding is myelin pathology which is especially severe at 2 weeks distally and 4 weeks proximally. A lot of abnormal myelin signal in the distal segment at 4 weeks is in the form of residual small myelin fragments. Note the prominent presence of astrocytes in the proximal segment that have transformed into hypertrophic, reactive profiles in (FIG. 4B) (asterisks). Scale bar: 10 μm
Figures 5A, 5B, 5C:
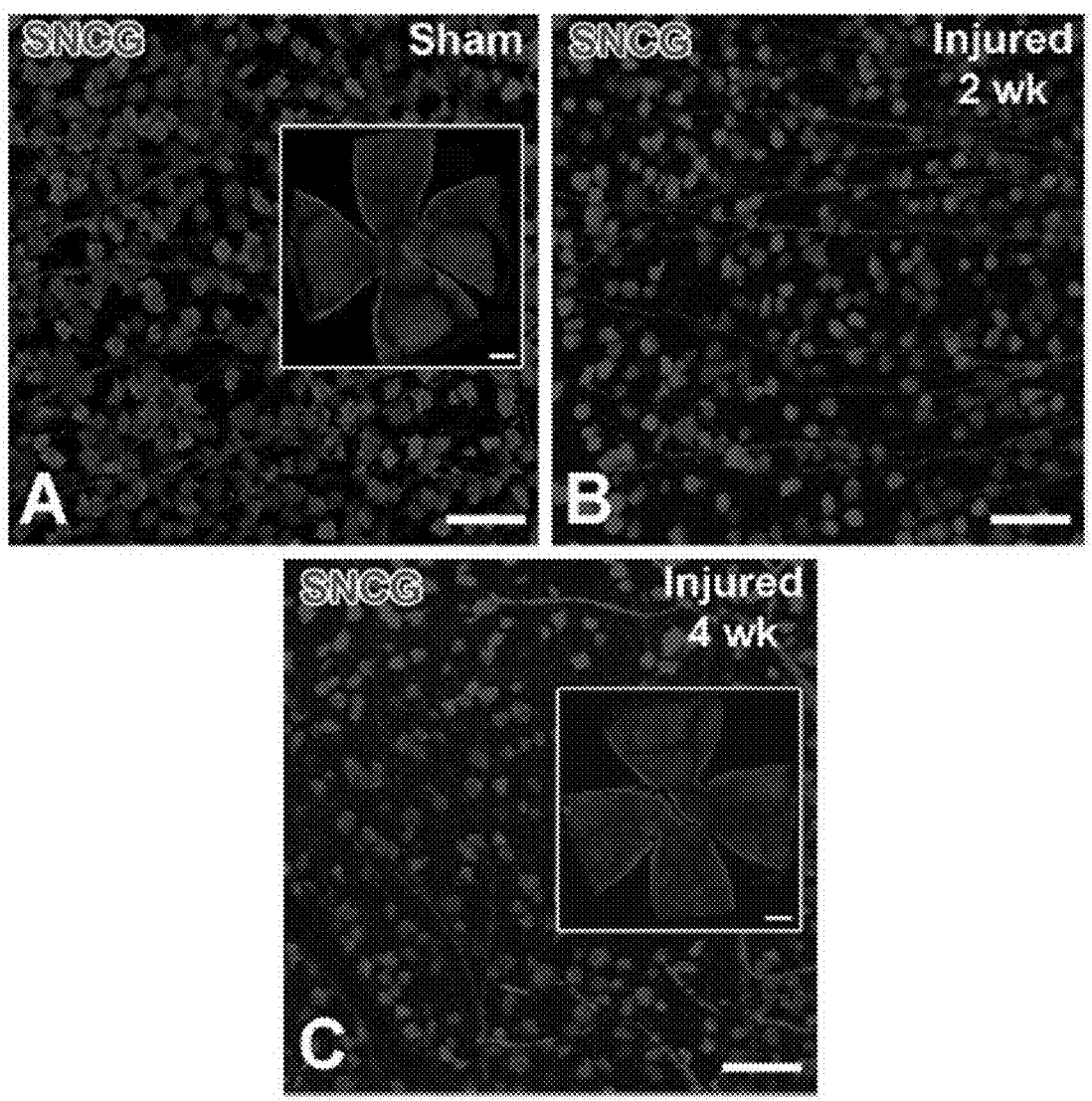
FIGS. 5A-5D show progressive RGC loss after IA injury. In these whole-mount retinas stained with the RGC marker γ-synuclein (SNCG) 2 or 4 weeks after sham (FIG. 5A) or IA injury (FIGS. 5B and 5C), there is evident RGC loss. Insets in FIGS. 5A and 5C show the retinal flat mounts from which images in main panels originated. Note the progressive decrease in cell density from FIGS. 5A and 5C.
Figure 5D:
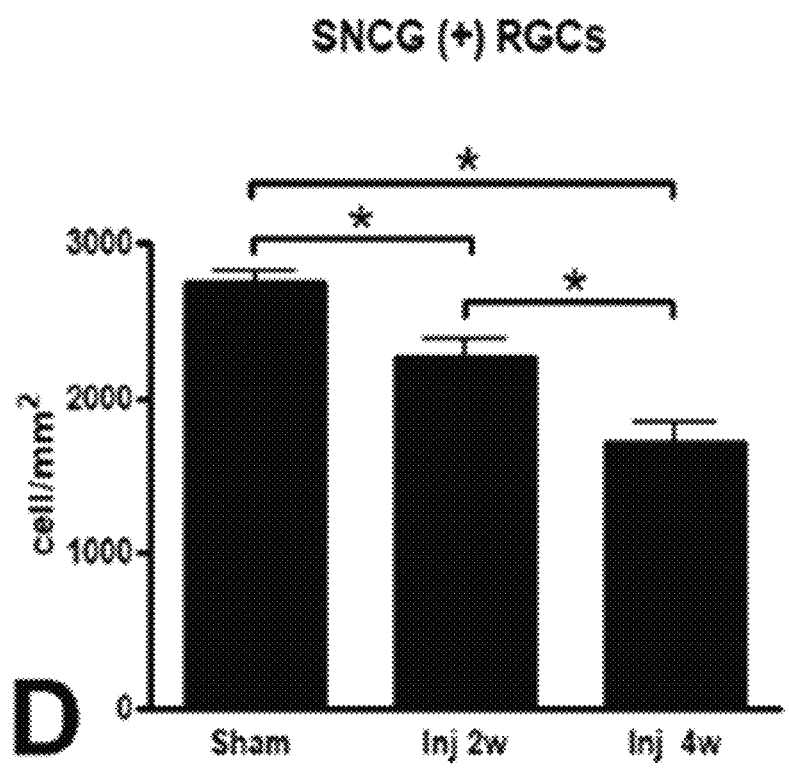
Figures 6A, 6B, 6C, 6D, 6E, 6F:
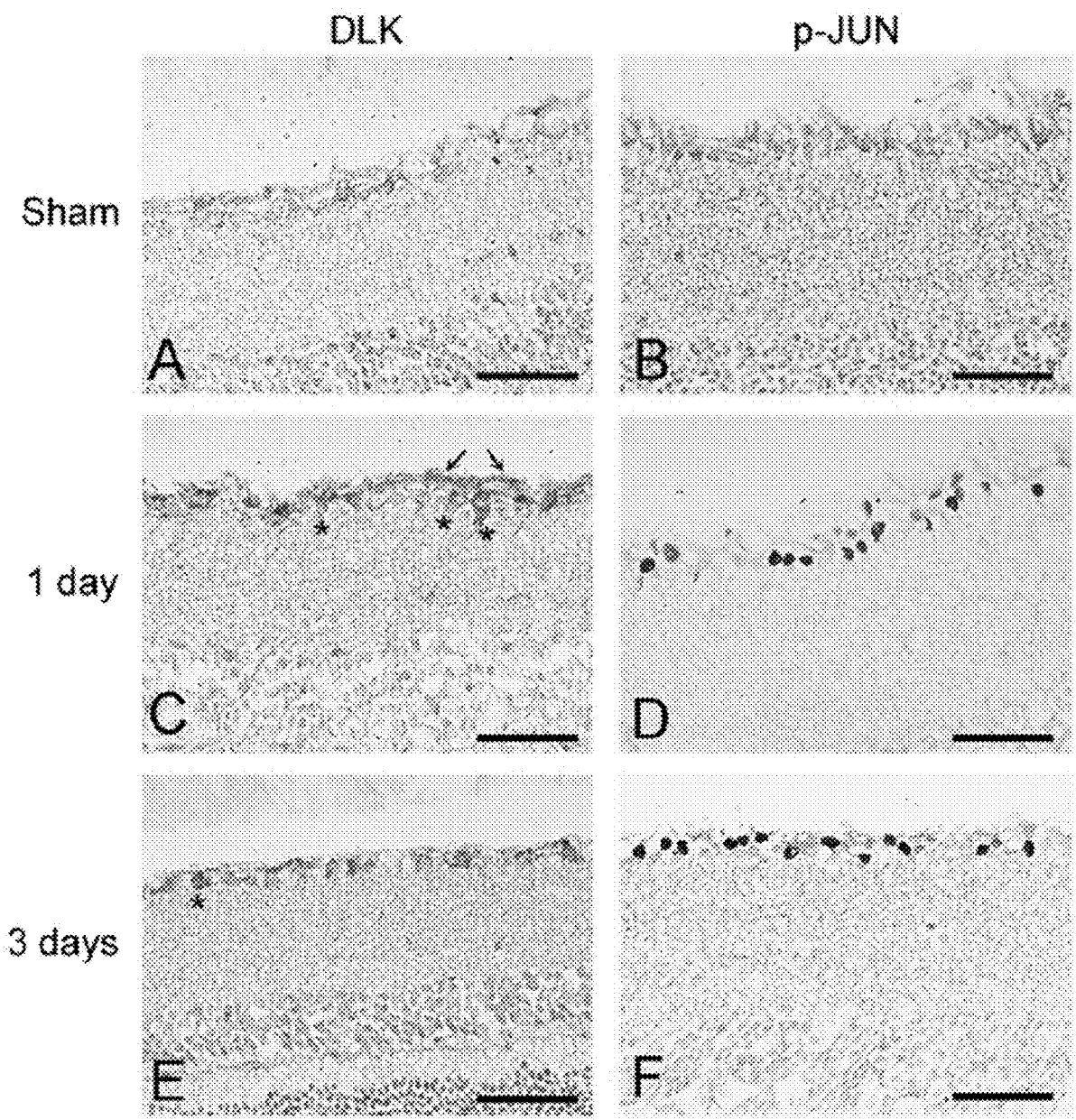
FIGS. 6A-6F are images showing activation of the DLK-JNK axis in the retinas of IA-injured mice.

Traumatic axonal injury in the visual system is associated with RGC axonopathy and axonal degeneration To characterize the initial effect of IA on the optic nerve, sections were immunostained for amyloid precursor protein (APP), a marker of early TAI. As early as 4 h after injury, a distinct region of APP-positive swellings and bulbs was found between the orbital apex and the chiasm (FIGS. 1A-1C). Amyloid precursor protein colocalized with IgG immunoreactivity, indicating serum extravasation and blood-brain barrier (BBB) disruption (FIGS. 1B-1C). Axonal abnormalities included classical axon bulbs and varicosities (FIGS. 1E-1F). When retinas were injected with CTB488 and optic nerves processed with CLARITY to visualize transport in the nerve, CTB488 transport blockade was identified in the same location of the nerve that had APP positive axonal abnormalities (FIGS. 1D and 1G). These findings indicate that IA produces a focal traumatic injury to RGC axons in the intracranial portion of the optic nerve. Seven days after injury, Gallyas silver staining revealed extensive axonal degeneration, from the optic nerve and tract to the superior colliculus (FIGS. 2A-2D). Degeneration was associated with the presence of deramified/hypertrophic microglia (FIGS. 2E-2F). Semithin sections of the optic nerve revealed numerous degenerative ovoids and axonal loss at 2 weeks post-injury that was maintained at 4 weeks (FIGS. 3 and 4). Axonal degeneration profiles differ between the proximal part of the nerve, close to the eye, with the distal part of the nerve, close to the chiasm. The distal nerve has more pronounced dysmyelination and more severe axonal loss compared to proximal both at two- and four-weeks post injury. There is ongoing degeneration in the distal segment between two- and four-weeks post injury (FIG. 3D). At 4 weeks, de- and dys-myelination were less evident distally, but there was extensive myelin debris (FIG. 4C). To determine if IA caused RGC death, the number of SNCG-positive cells was counted in retinal flatmounts two- and four weeks post-injury and a progressive decrease in the number of RGC somas was found in the course of the first month (FIG. 5). Taken together, these results suggest that the IA model produces a focal axonal injury that leads to progressive axonal and somal RGC degeneration.

Figure 7:
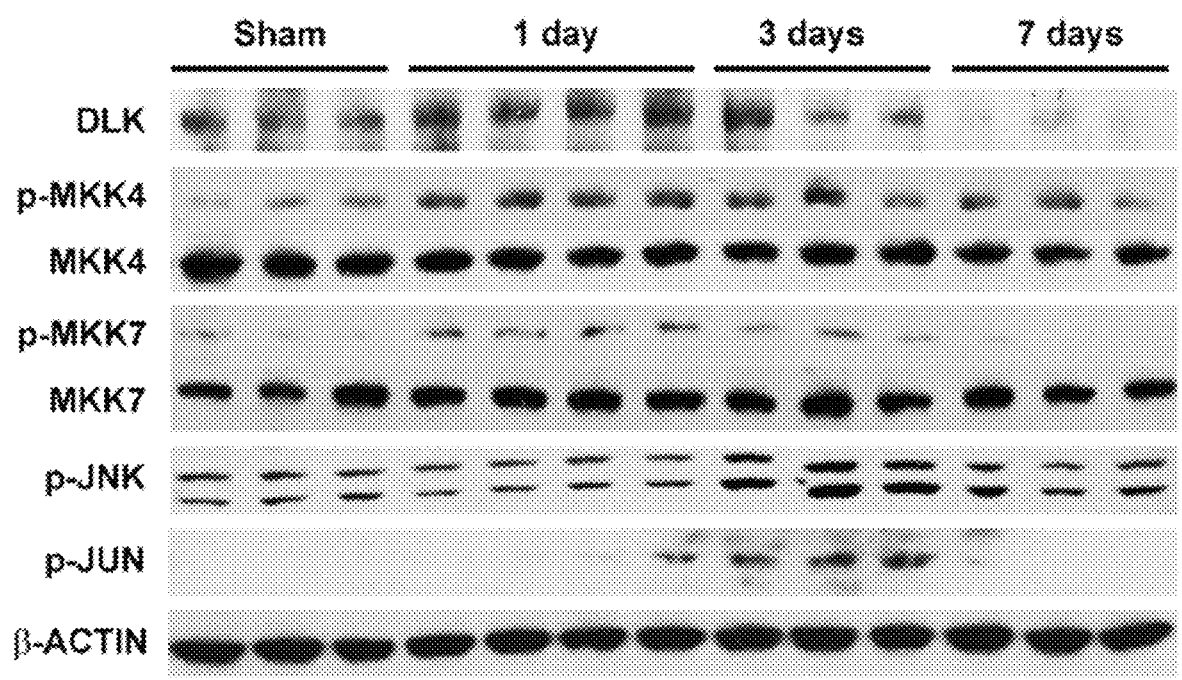
FIG. 7 shows the expression of kinases in the DLK-JNK pathway in the retina after IA injury by western blotting. Bar graphs represent quantitation of the intensity of protein bands for DLK, activated MKK4 and MKK7 ratios, p-JNK and p-JUN in the sham condition and at 1, 3, and 7 days post-injury. Data were analyzed with one-way ANOVA followed by Tukey's post hoc test. * $p<0.05$
Figures 8A, 8B, 8C:
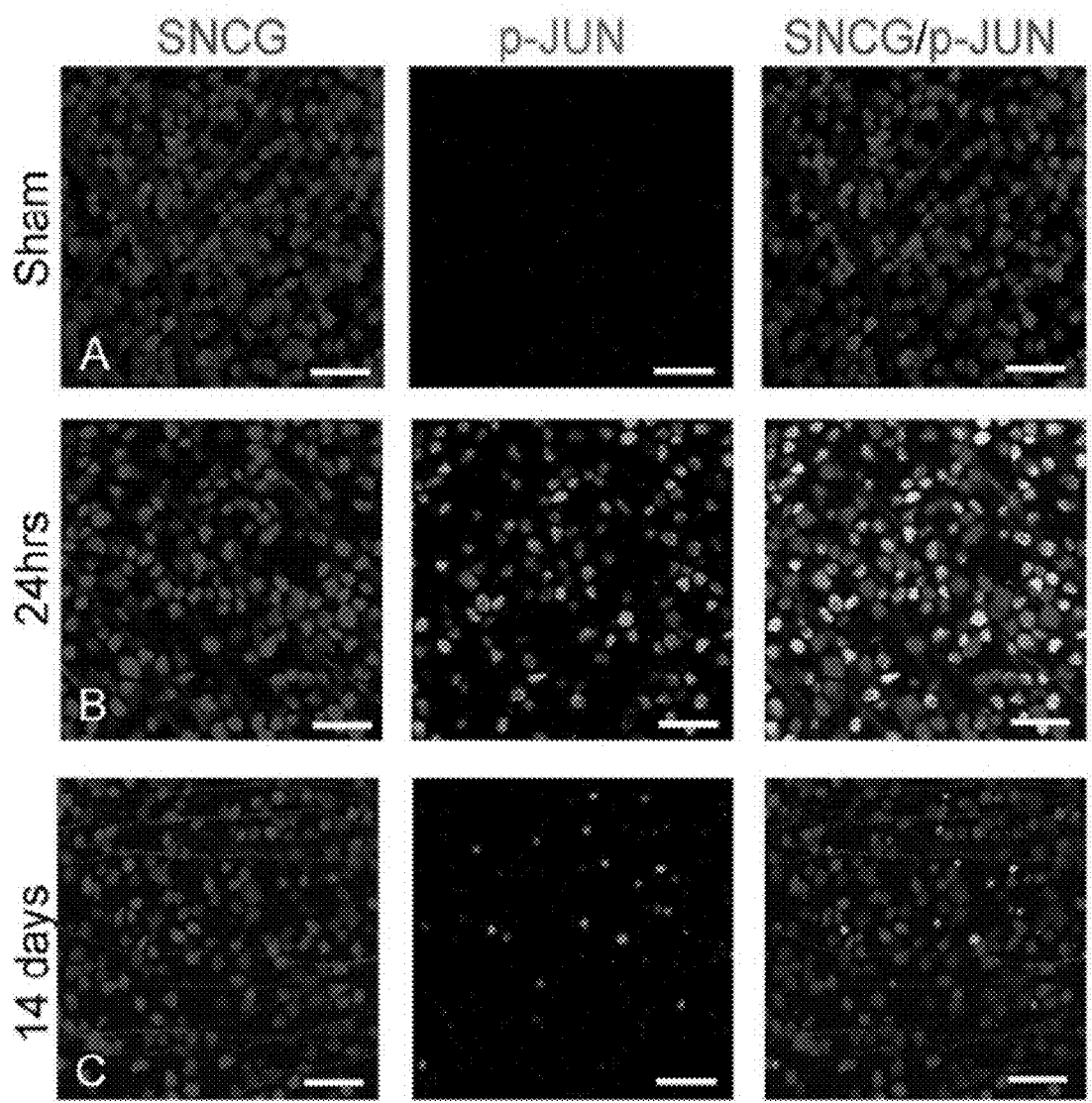
FIGS. 8A-8E show quantitative assessment of DLK-JNK activation after IA injury based on counts of p-JUN (+) RGCs.
Figures 8D, 8E:
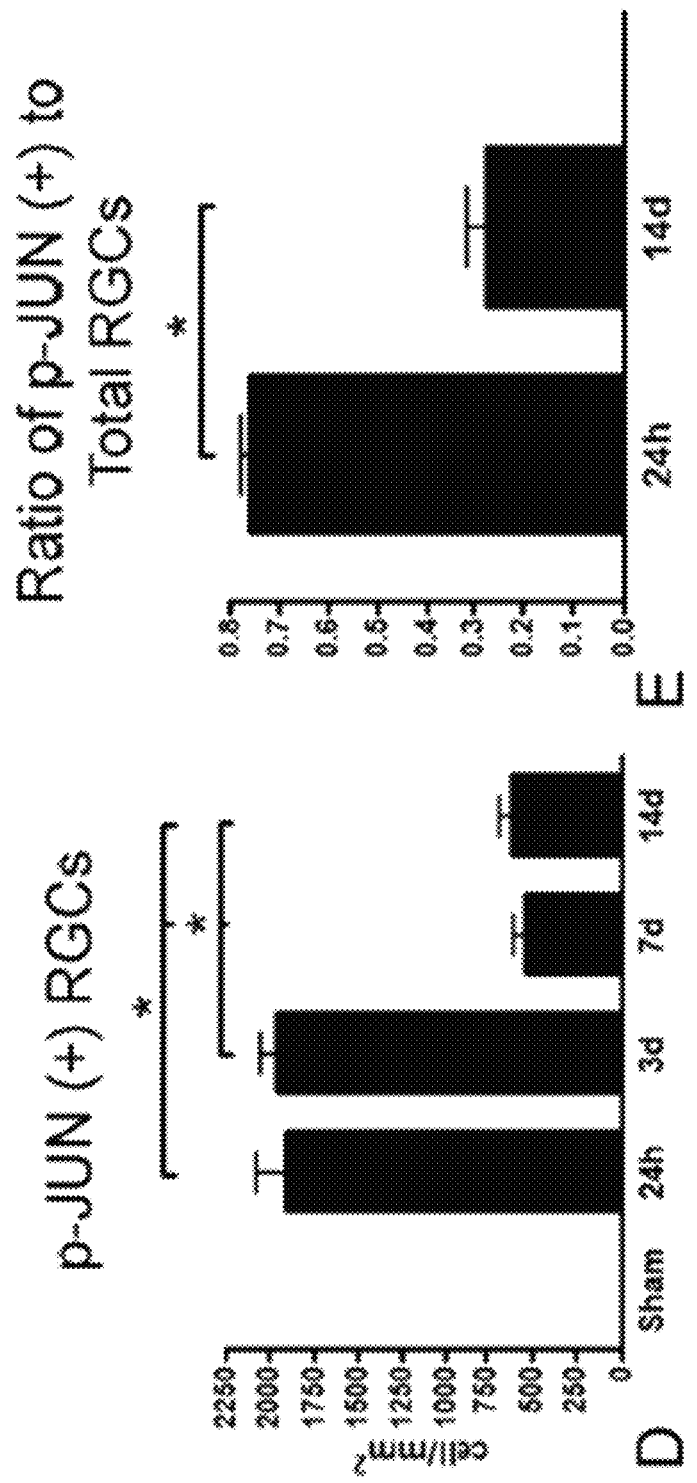

The DLK-JNK pathway is activated in RGCs in the course of visual TAI. Based on previous work implicating DLK-JNK signaling in RGC degeneration after optic nerve crush, it was tested whether a diffuse TBI model such as IA activates the DLK-JNK cascade in a similar fashion. Since DLK levels are indicative of pathway activation, retinal sections were immunostained for DLK and also immunoblotted whole retinal lysates. Both approaches showed transient upregulation of DLK, peaking around 1 day after injury (FIGS. 6A, 6C, 6E, and 7). LZK IHC or immunoblotting was not pursued because of the lack of reliable antibodies. To determine if this upregulation was associated with pathway activation, immunoblotting and IHC were used to measure the phosphorylation state of the downstream kinases MKK4, MKK7, JNK1-3, and the transcription factor JUN. By 1 day and extending at least until day three after injury, increased phosphorylation of each of the DLK substrates, MKK4 and MKK7, was evident (FIGS. 6B, 6D, 6F, and 7). The time course of the activation was slightly different between IHC and immunoblotting, with whole-retina immunoblotting failing to detect the early increase likely because of the scarcity of RGCs in whole-retinal samples. Nonetheless, both techniques showed a robust activation of JUN after injury that returned to near baseline by 1 week (FIG. 7). One confounding possibility is that RGCs with active DLK signaling may die, thereby explaining the transient kinase activation. To test this hypothesis, retinal whole-mounts were double stained with antibodies against p-JUN for pathway activation and the RGC marker SNCG for viable neurons. The increased density of p-JUN positive RGCs at one, three, seven, and 14 days after IA injury confirmed activation of the DLK-JNK axis (FIG. 8). Moreover, between one and 14 days, there was a decrease in the number of live RGCs with JUN activation, suggesting that kinase activation is transient for most RGCs. Because this TBI model initially activates DLK-JNK signaling in 75% of RGCs (FIG. 8D), but ultimately only ~40% of RGC somas and axons die (FIG. 5), it is likely that some fraction of RGCs is able to recover from the injury and normalize the DLK signal. Retinal ganglion cells with prolonged p-JUN expression appear atrophic and with decreased SNCG expression, an indication that they may be degenerating neurons. This potential recovery is surprising given that activation of the DLK-JNK pathway in the optic nerve crush model is sustained and leads to death of most RGCs [17]. In contrast, TBI leads to a robust initial activation of the DLK-JNK pathway, which is partially reversed in the post-acute phase of injury in surviving RGCs.

Figures 9A, 9B, 9C, 9D:
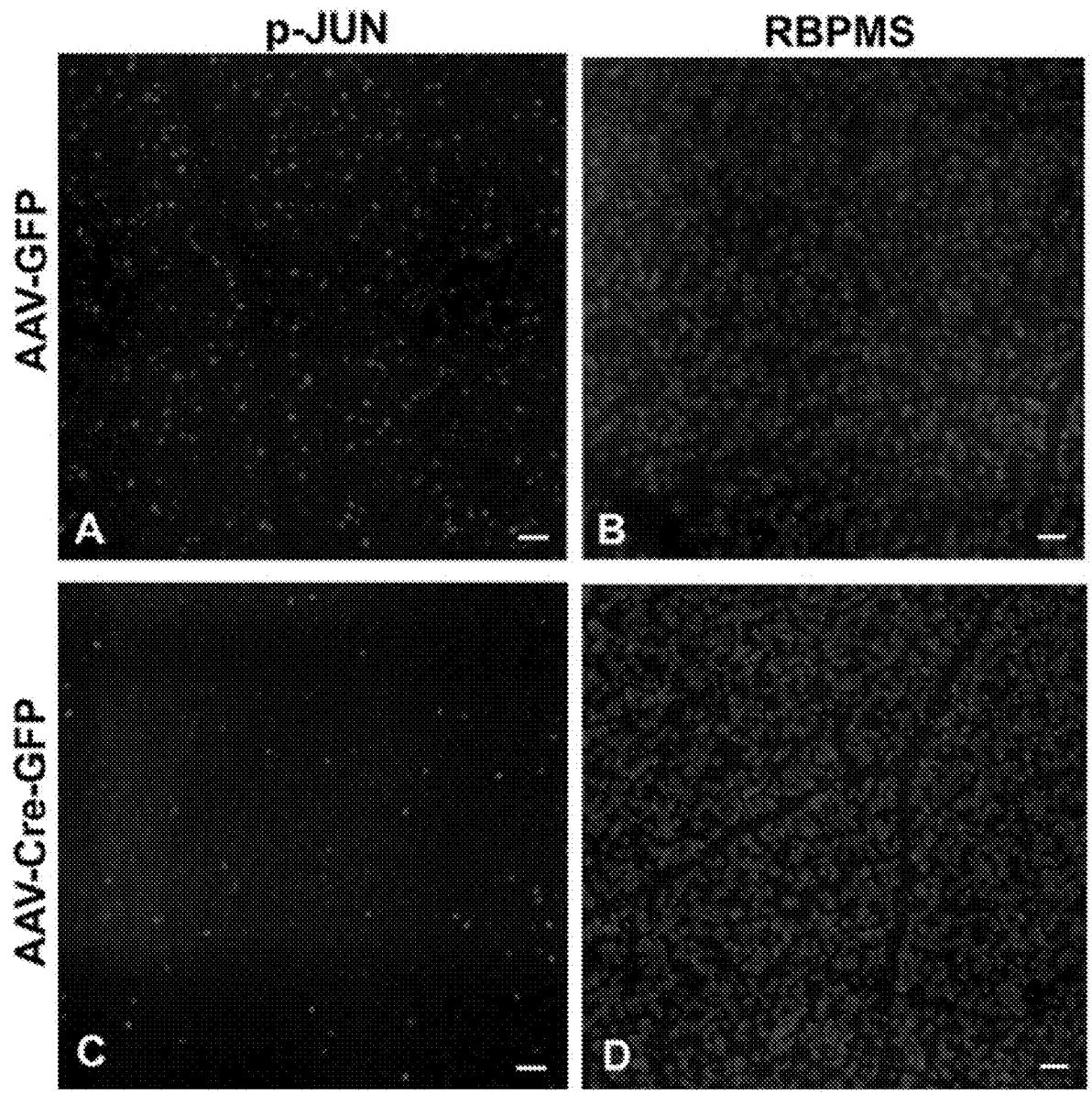
FIGS. 9A-9H show the effects of Dlk or combined Dlk/Lzk deletion on JNK signaling and RGC survival after IA injury. Subjects were Dlkfl/fl or Dlkfl/flLzkfl/fl mice. As elsewhere in this paper, p-JUN expression was used as a marker of DLK-JNK activation. Retinal ganglion cells were labeled with RBPMS.
Figures 9E, 9F, 9G, 9H:
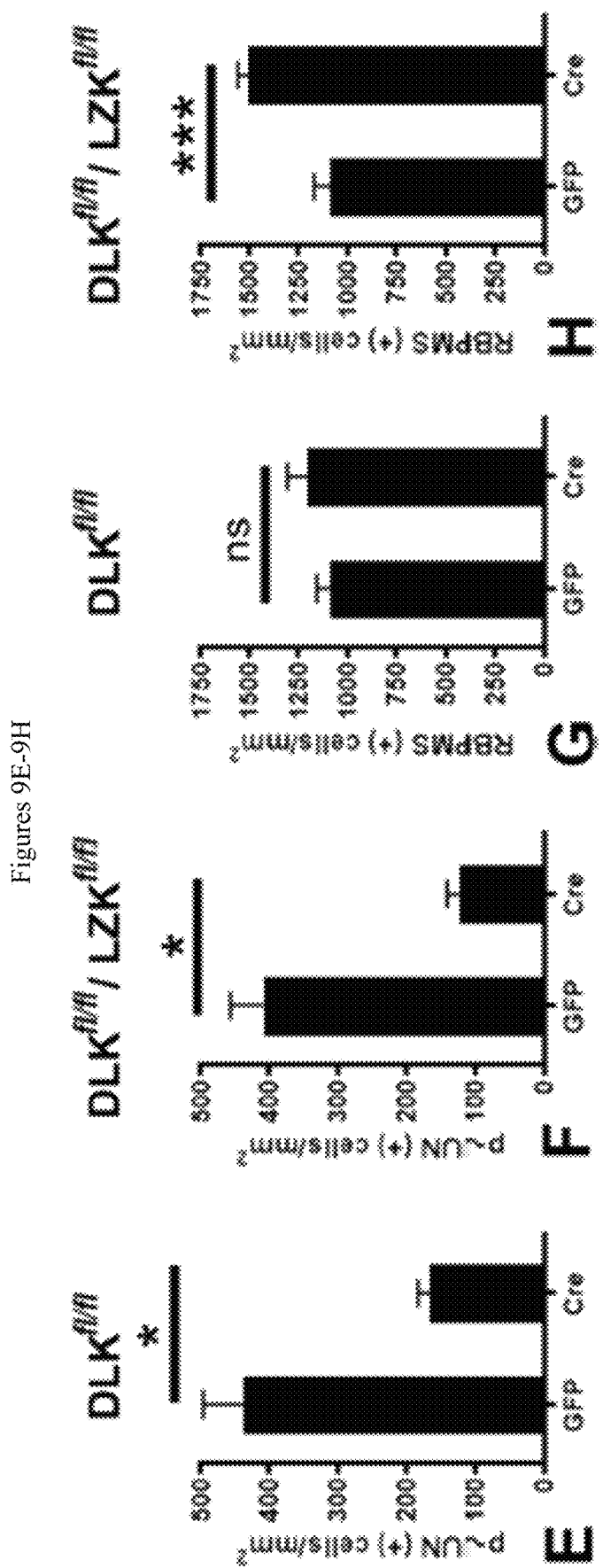

The activation of JUN in visual TAI is dependent on DLK signaling. It was previously shown that DLK is the major MAP3K input responsible for JNK activation in response to axotomy in the optic nerve crush model, with additional contribution from LZK [18, 19]. To explore the degree to which the same kinases are responsible for JNK activation following the nontransecting injury in the IA model, mice with conditional alleles of Dlk and Lzk [18, 22] were tested. Floxed Dlk or floxed Dlk/Lzk ($Dlk^{fl/fl}$ and $Dlk^{fl/fl}Lzk^{fl/fl}$ mice, respectively) were intravitreally injected with AAV-Cre into one eye and a control virus (AAV-GFP) into the fellow eye. After 2 weeks, time sufficient for AAV to complete its lifecycle and trigger recombination, mice were subjected to TBI with IA. The rate of JUN phosphorylation was then determined by the number of p-JUN (+) RGCs 3 days after injury (when signaling peaks based on immunohistochemical and immunoblot data). Compared to control animals (FIG. 9A), eyes with a targeted disruption of DLK/LZK had a significant (~75%) suppression of JUN phosphorylation (FIGS. 9C and 9F). Interestingly, similar suppression was seen with DLK disruption alone (FIG. 9E), suggesting that DLK is a primary mediator of JNK activation in the IA model, and that LZK cannot compensate for a loss of DLK.

Figure 10A:
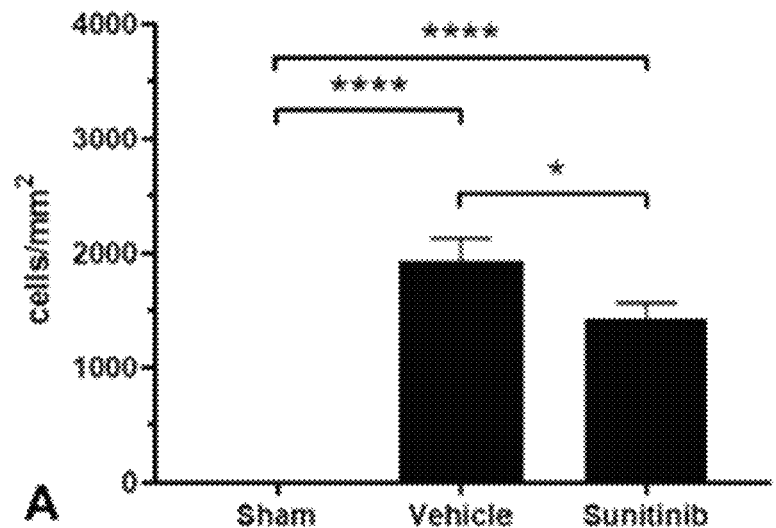
FIGS. 10A and 10B are graphs of the suppression of JNK signaling and promotion of RGC survival by sunitinib in the IA model.
Figure 10B:
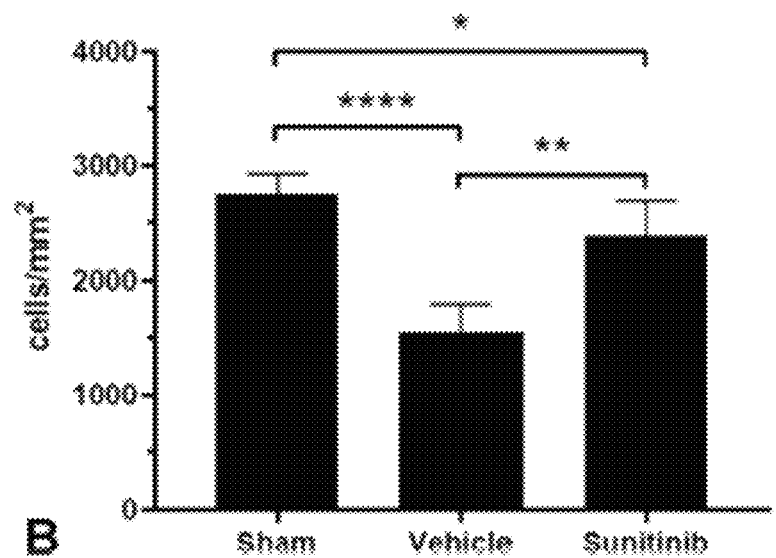
Figures 11A, 11B:
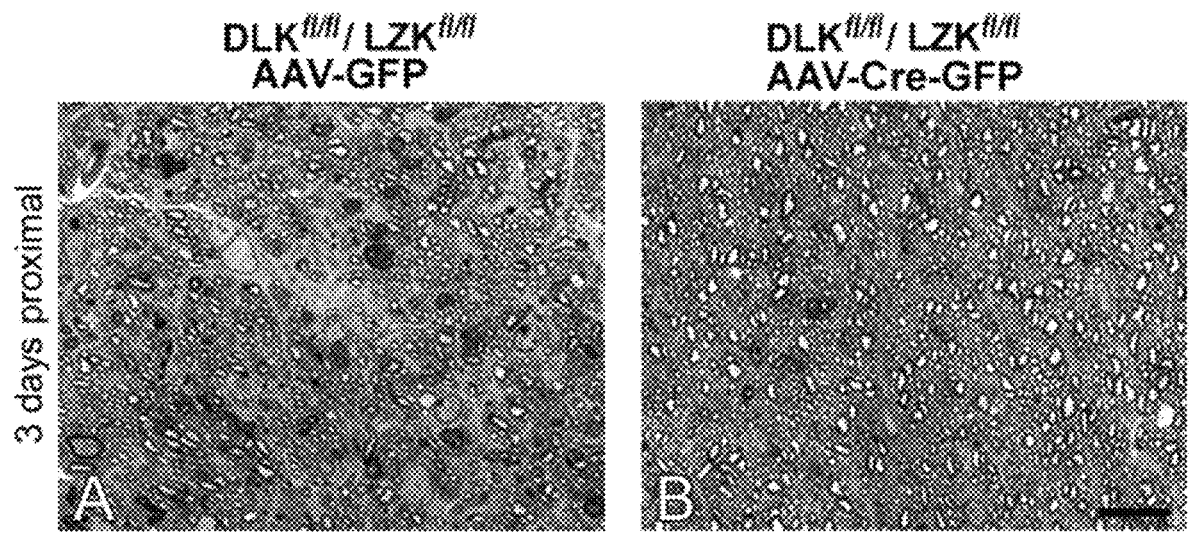
FIGS. 11A-11J show combined Dlk/Lzk deletion using Dlkfl/flLzkfl/fl mice delays axonal degeneration in the optic nerve.
Figures 11C, 11D, 11E, 11F, 11G, 11H, 11I, 11J:
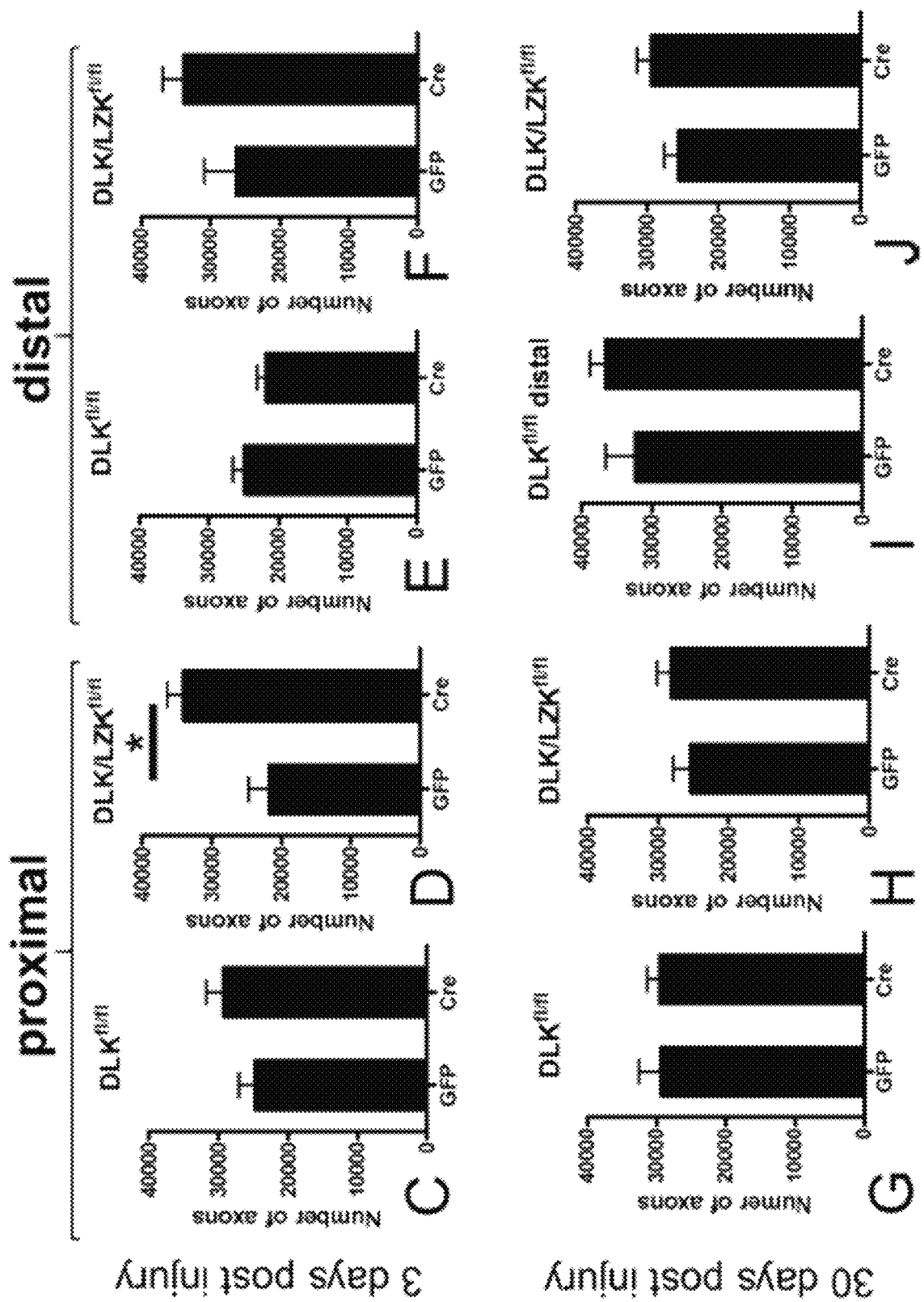

Combined deletion of Dlk and Lzk increases survival of RGCs in visual TAI. To test the role of DLK and LZK in cell death following IA, a separate group of Dlkfl/fl and $Dlk^{fl/fl}Lzk^{fl/fl}$ mice were injected with AAV-Cre or AAV-GFP and RGC survival was quantified 30 days after injury. Deletion of Dlk failed to show a significant effect on survival (FIG. 9G). However, combined deletion of Dlk and Lzk was protective and significantly increased survival of RGCs (FIGS. 9B, 9D, 9H). These findings suggest that DLK and LZK have redundant abilities to trigger cell death in TAI, which differs from the ONC model in which Dlk deletion alone is robustly protective [18]. Pharmacologic DLK/LZK inhibition improves RGC survival in visual TAI. Since genetic disruption of DLK/LZK protected injured RGCs, it was hypothesized whether pharmacological inhibition of DLK and LZK could similarly improve RGC survival in the IA model. Using published profiling data, the FDA-approved protein kinase inhibitor sunitinib was identified as having activity against DLK and LZK, but not against the downstream kinases MKK4, MKK7 and JNK1-3 [30]. Given that sunitinib penetrates the CNS [31], it was tested whether its administration could promote RGC survival in the IA model. First, to confirm target engagement, mice were treated with intraperitoneal sunitinib (or the vehicle control) at 1 day and 4 h prior to injury, and then once more on the day after injury. Retinas were then harvested and stained for p-JUN. Sunitinib treatment led to a significant decrease in the number of p-JUN positive RGCs, confirming that it was able to partially suppress JNK signaling (FIG. 10). The experiment was repeated, this time extending the treatment period for 21 days and assaying for RGC survival using SNCG staining of retinal whole-mount preparations. The results show that sunitinib treatment can improve neuronal survival following IA, increasing the number of surviving RGCs from 1500 cells/mm2 to nearly 2300 cells/mm2 ($p<0.05$, t-test) when compared to vehicle, although the effect does not achieve normal (sham) RGC densities (FIG. 10B). Combined deletion of Dlk and Lzk protects optic nerve axons early in the course of TAI-associated axonopathy. Having established the long-term protective effect of either genetic or pharmacological DLK/LZK inhibition on RGC survival, the role of these kinases was explored in axonal degeneration produced by the IA model. Based on stereological counts of myelinated axons in the optic nerve proximal and distal to the putative site of injury and comparisons between AAV-Cre and control AAVGFP-treated eyes, DLK deletion alone did not appear to protect axons at 3 or 30 days post-injury. The combined deletion of Dlk and Lzk protected optic nerve axons at 3 days after TBI, but this effect was not sustained at the 30-day time point post injury (FIG. 11). Taken together, these results suggest that TAI-associated axonal degeneration in the visual system is not as dependent on the DLK/LZK genetic program.

Discussion

This study explores the role of two MAP3Ks, DLK and LZK, in TAI-associated axonopathy and RGC degeneration in the visual system following IA injury. Traumatic axonal injury in the visual system is featured by axonal transport defects followed by axonal swellings and bulbs in a segment of optic nerve. This is then followed by progressive axonopathic changes (traumatic axonopathy) leading to degeneration of a sizable portion of axons and retrograde death of RGCs. These findings indicate that TAI in the visual system is associated with the activation of the DLK/LZK-JNK axis that is responsible, at least in part, for RGC somal death, although its role in axonal degeneration is limited. The conditional knockout of Dlk and Lzk in adult mice employed here precludes a neurodevelopmental compensation effect on RGC survival and points to the central role of the DLK-JNK axis in neurodegeneration after TBI. The role of DLK/LZK in triggering RGC degeneration during TAI is further supported by the neuroprotective effect of the FDA-approved kinase inhibitor, sunitinib, a finding with therapeutic potential. These results show that molecular signals operating in simple forms of axonal injury, e.g., axotomy, play important roles in some of the degenerative outcomes of TAI in the CNS.

It was previously shown that this diffuse model of TBI (IA) leads to multifocal TAI in the corticospinal tract, optic nerve, gracile fasciculus, fornix, and corpus callosum [11, 12]. Traumatic axonal injury in the visual system is associated with optic nerve axonopathy (traumatic axonopathy) that is further characterized here and has been shown to correlate with injury burden [11]. The primary biomechanical disruption of the optic nerve corresponds to a region between the orbital apex and the chiasm which is roughly used for the pathological distinctions between "proximal" and "distal" in this paper. Degenerating optic nerve axons show widespread dysmyelination/demyelination that is evident as early as 3 days post-injury. Axonopathy is more severe distal to the site of biomechanical disruption where it continues to evolve over the course of the 4-week period examined in this study. Compared to the effects of IA in other CNS tracts, e.g., the corticospinal tract, a distinct feature of TAI in the optic nerve is the retrograde degeneration of neurons (RGCs), in keeping with the classical vulnerability of these nerve cells to death after axonal lesions [32-34]. This notion is further supported by the fact that progression of death of RGC somata appears to lag behind the wave of axonal degeneration. The co-registration of rates of death in RGCs and in proximal axons, both of which are ~25-30%, may suggest a biological correlation between degeneration of perikarya and degeneration of proximal axons.

DLK is part of a highly-conserved retrograde injury signal that is triggered by axotomy, leading to the activation of both apoptotic and regenerative processes [17, 19, 21, 35]. However, simple axotomy models (e.g., optic nerve crush) differ from more clinically relevant models, e.g., TAI, in that the latter tend to produce more graded and incomplete axonal injury. The degree to which DLK is required for TBI- and TAI-associated axonopathy had not been previously explored. These results suggest some key similarities and differences. As with axotomy, TAI leads to upregulation of DLK and activation of the MKK/JNK/JUN signaling pathway in RGCs. Moreover, DLK acts as obligatory upstream mediator of JUN activation, because targeted disruption of DLK leads to a near-total suppression of JUN phosphorylation. Perhaps the most important difference is that the TAI model triggers DLK activation in such a way that a subset of RGCs can recover and terminate the signal. The mechanism by which this phenomenon occurs is probably related to subthreshold biomechanical injury in a large number of optic nerve axons but may also involve selective vulnerability of subclasses of RGC neurons. These issues need to be explored further because they may have important implications for RGC neuroprotection in the context of TBI.

Furthermore, in contrast to axotomy models in which deletion of Dlk by itself rescues the survival of ~75% of RGCs [16, 17, 19] in the TAI model, knockout of Dlk has little effect on RGC survival. Only when both DLK and LZK were targeted was an increase in RGC survival observed, suggesting a degree of genetic redundancy for these two highly-related kinases. Not surprisingly, the degree of redundancy seems to be dependent on the model, with the TAI model and primary RGC cultures showing a large degree of DLK/LZK redundancy (e.g., combined inhibition is required for robust survival), while the ONC model shows a lesser degree of redundancy (e.g., combined disruption produces a more modest increase in survival over Dlk disruption alone). It is also interesting to note that deletion of Dlk with or without Lzk leads to a significant reduction in the downstream phosphorylation of JUN but only the combined deletion of the two protects RGC viability. Although effects on the kinetics or localization of JNK activation cannot be excluded, these data could indicate that LZK may be upstream of an as-yet-unidentified pathway responsible for RGC cell death in TAI.

In order to develop an expedited route to clinically evaluate DLK/LZK inhibition as a neuroprotective strategy, FDA-approved protein kinase inhibitors were surveyed for ones with activity against DLK and LZK. This approach identified sunitinib (Sutent®), FDA-approved for renal cell carcinoma and gastrointestinal stromal tumor, as having high nanomolar IC50 for both DLK and LZK. Moreover, it was shown that sunitinib increased the survival of induced pluripotent stem cell (iPSC)-derived human RGCs [18]. These findings have been extended to demonstrate that pharmacological blockade of DLK and LZK with sunitinib increases RGC survival in vivo in a rodent TBI model. With the possible exception of antioxidants [36], this is the first demonstration of an FDA-approved compound decreasing neuronal cell death in a TBI model.

Central nervous system tracts other than the visual system that are vulnerable to TAI and succumb to traumatic axonopathy [12] may also use DLK-dependent injury signals; therefore, these findings raise the prospect of using protein kinase inhibitors as part of a neuroprotective strategy for TBI. Traumatic brain injury very commonly affects axons and the state of axons after injury is important for the integrity of neuronal circuitry and the function of neural networks [37]. After it was established that RGC somatic death is, at least in part, a DLK/LZK dependent phenomenon, the effects of the DLK/LZK pathway on axonal survival were explored. DLK appears to be implicated in axonal degeneration through a negative effect on levels of SCG10, an anterogradely transported protein that promotes axonal survival after axotomy in vitro [38]. More recently, the involvement of DLK in axonal degeneration has been examined in vitro using primary dorsal root ganglion neurons [23]. These experiments have revealed an important role of DLK in maintaining basal levels of NMNAT2, an essential axonal survival factor, through the degradation of the palmitoylated form of the enzyme under normal conditions. Deletion of Dlk raises basal level of anterogradely transported NMNAT2 prior to injury, and thus delays axonal degeneration. This protective effect is more pronounced when combined with deletion of the Phr1/Skp1a/Fbxo45 ligase complex that is important for the degradation of the nonpalmitoylated fraction of NMNAT2 [23]. Consistent with these observations, it was found that the combined deletion of Dlk and Lzk only protected optic nerve axons from degeneration early, e.g., 3 days, post injury. This is the first demonstration that LZK plays a role, albeit limited, in an active axonal degeneration program. This finding is in line with the kinetics of NMNAT2, a labile protein that needs continuous replenishment to exert protective effects on axons [39]. The blockade of anterograde transport that occurs with TAI would have prevented the axonal transport of NMNAT2, leaving the axon only with basal levels of the protein, which may be higher is neurons with deleted Dlk/Lzk. This effect, however, may not be sufficient to completely protect injured axons, as suggested by the fact that there is no significant effect on survival at 30 days post injury.

Conclusion

The above experiments show that the RGC loss after TBI can be prevented, at least in part, by the genetic deletion or pharmacological inhibition of DLK/LZK. This finding may be an important step in protecting RGCs in the context of TBI and potentially allowing them to reintegrate into the visual circuitry if many axons are still relatively intact or if regenerative strategies become more effective in the future [40]. The experiments also show that by blocking DLK/LZK degeneration of RGC axons may be delayed although, as has been also shown in simple axotomy lesions, the effect on RGC somata is clearly more robust [16, 41-43]. Finally, these experiments show that an FDA-approved drug, sunitinib, with activity against both DLK and LZK, is able to increase RGC survival in a TBI model.

Example 2

This example demonstrates that combined MAPK and NAMPT inhibition results in greater efficacy in axonal degeneration.

The role of the DLK/LZK MAPK pathway in regulating NAD and SARM1 pathways of axonal degeneration was established. Its role in regulating levels of the NAD-synthesizing enzyme NMNAT2 after injury was explored by treating murine DRG axons with the DLK/LZK inhibitor GNE-3511 after axotomy.

Figure 12:
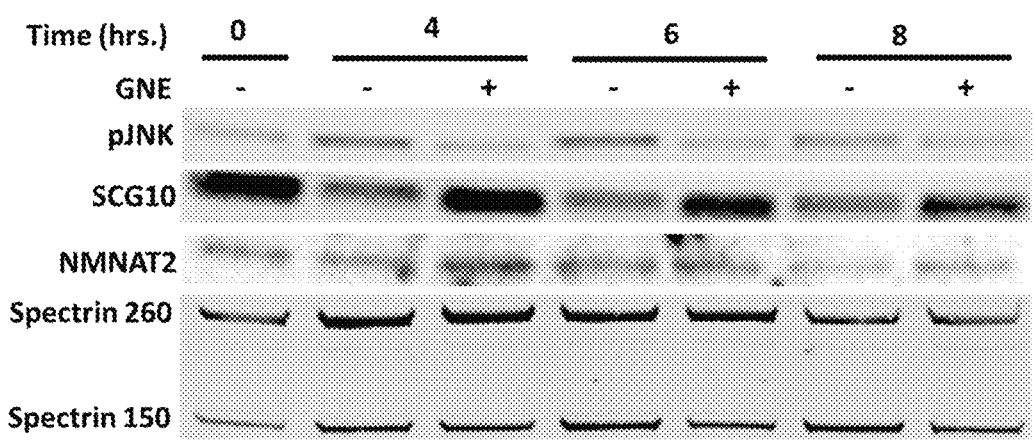
FIG. 12 is a western blot analysis showing that GNE-3511 treatment immediately after axotomy, reduced phosphorylation of the downstream JNKs (validation of its inhibitory effect on the cognate pathway) and of the axonoprotective SCG10 (validation of its inhibitory effect downstream of the cognate pathway) reduced the degradation of NMNAT2 (parallel effect on the NAD synthesis pathway) and ameliorated the calpain-mediated degradation of α-Spectrin (positive effect on axonal breakdown). Data show that inhibiting the MAPK cascade also has effects on the NAD synthesis pathway.

Western blot analysis revealed that GNE-3511 treatment immediately after axotomy reduced phosphorylation of the downstream JNKs (validation of its inhibitory effect on the cognate pathway) and of the axonoprotective SCG10 (validation of its inhibitory effect downstream of the cognate pathway), reduced the degradation of NMNAT2 (parallel effect on the NAD synthesis pathway), and ameliorated the calpain-mediated degradation of α-Spectrin (positive effect on axonal breakdown). Data show that inhibiting the MAPK cascade also has effects on the NAD synthesis pathway (FIG. 12).

Figure 13:
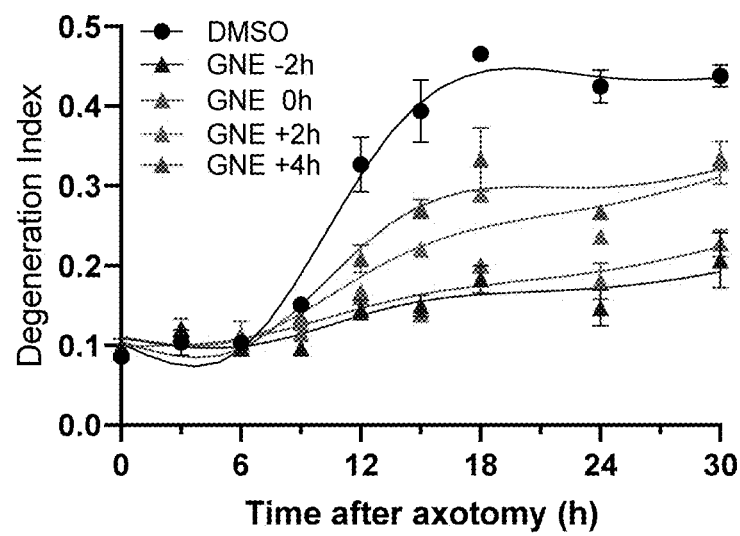
FIG. 13 is a graph showing significant protection with application of GNE-3511 before or immediately following injury and lesser protection in more delayed regimes. Data show that MAPK inhibition alone has effects on axonal degeneration when applied early post-injury.

To assess the therapeutic potential of post-axotomy MAPK inhibition, axons were treated with GNE-3511 at different time points before or after axotomy (2 h pretreatment, immediately after axotomy, 0 h, or 2 and 4 hours post-injury). Significant protection was found with application of GNE-3511 before or immediately following injury and lesser protection in more delayed regimes. Data show that MAPK inhibition alone has effects on axonal degeneration when applied early post-injury (FIG. 13).

Figure 14A:
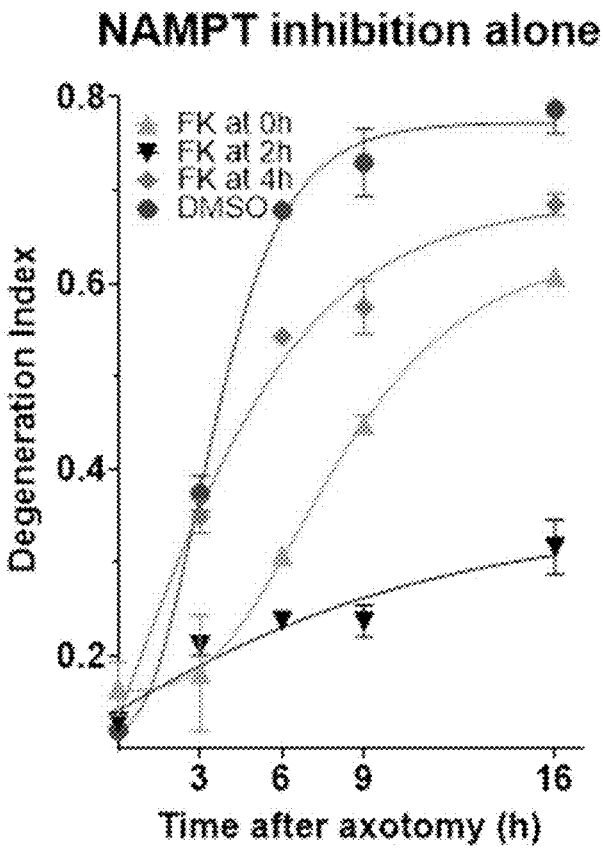
FIGS. 14A and 14B are graphs showing in the absence of GNE-3511, FK-866 provided protection especially when added at 2 hours (FIG. 14A). With the addition of GNE-3511, the effect of FK-866 treatment was enhanced at 2, 4 and 6 hours post injury (FIG. 14B). Data show a synergistic effect on axonal degeneration of DLK (applied at the time of injury) and NAMPT inhibitors applied at different time points after injury.
Figure 14B:
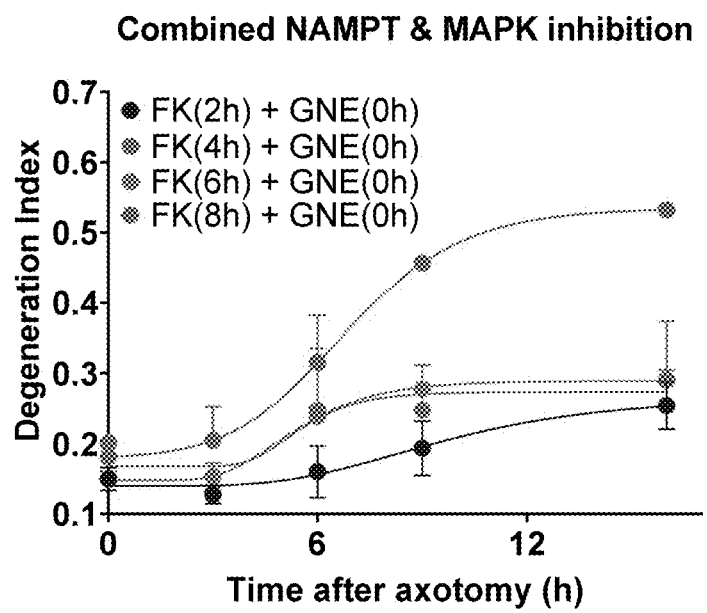

Due to the different mechanism of action of MAPK and NAMPT inhibition, therapeutic synergy was further tested by treating axotomized axons with the MAPK inhibitor GNE at the time of injury and the NAMPT inhibitor FK866 at different time points (2, 4, 6 or 8 hours post injury). In the absence of GNE-3511, FK-866 provided protection especially when added at 2 hours (FIG. 14A). With the addition of GNE-3511, the effect of FK-866 treatment was enhanced at 2, 4 and 6 hours post injury (FIG. 14B). Data show a synergistic effect on axonal degeneration of DLK (applied at the time of injury) and NAMPT inhibitors applied at different time points after injury (FIG. 14).

Example 3

Figure 15:
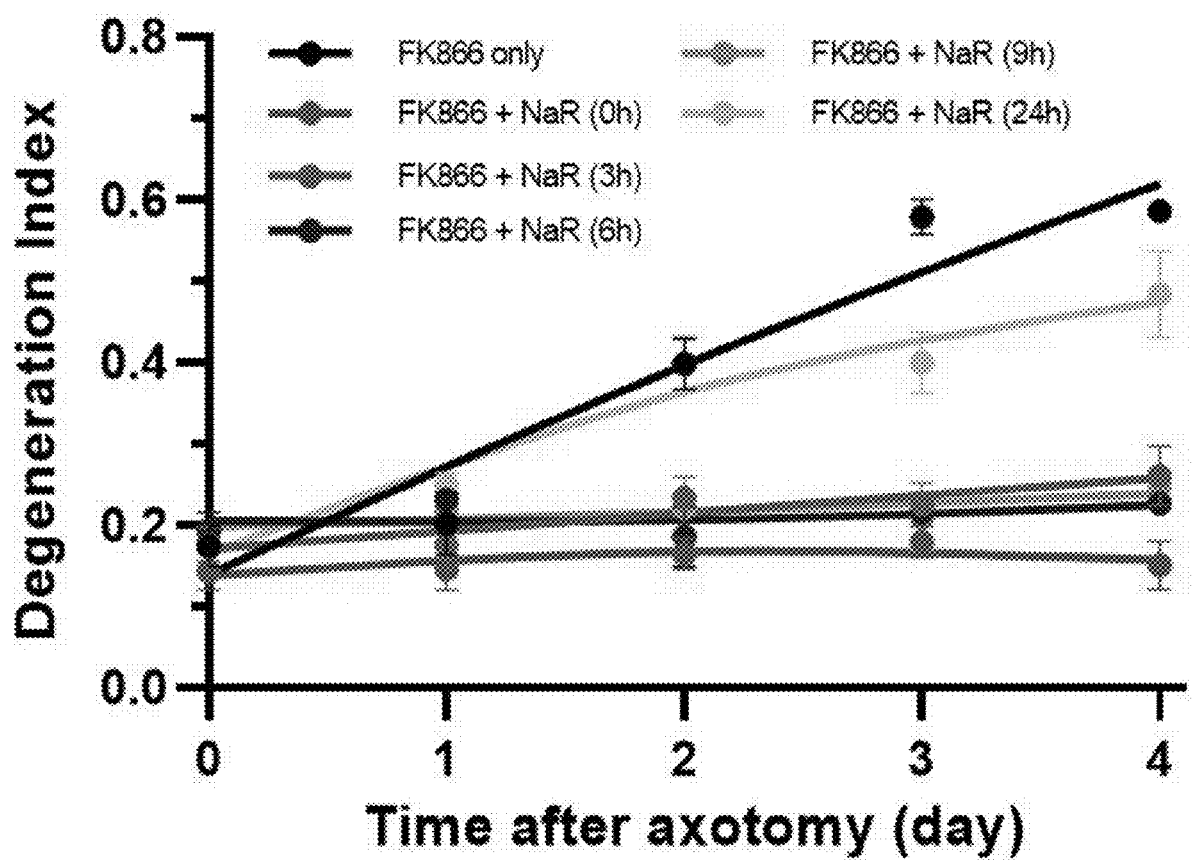
FIG. 15 is a graph showing NAMPT inhibition with NaR supplementation can be delayed up to 9 h after axotomy with no loss of efficacy in suppressing axon fragmentation. Transected axons were treated with the NAMPT inhibitor FK866 after injury and NaR was added concurrently or at 3, 6, 9, or 24 hours post axotomy.

This example provides data indicating that NAMPT inhibition with NAD+ precursor metabolite nicotinamide riboside (NaR) supplementation can be delayed up to 9 hours after axotomy with minimal and/or no loss of efficacy in suppressing axon fragmentation. Transected axons were treated with the NAMPT inhibitor FK866 after injury and NaR was added concurrently or at 3, 6, 9, or 24 hours post axotomy. Statistical analysis of degeneration index was performed by two-way ANOVA for the effect of time (F(4,32)=62.77, p<0.0001), treatment (F(5,8)=17.05, p=0.0004), and their interactions (F(20,32)=16.82, p<0.0001) with Holm-Šidák's multiple comparisons. Supplementation of NaR 3, 6, or 9 hours post-axotomy in the presence of FK866 significantly protected axons compared to treatment with FK866 alone (t(40)=8.0-11.85, p<0.0001) up to 4 days post-injury. Supplementation of NaR at 24 hours had no additive effect on FK866 treatment alone. See FIG. 15 (error bars indicate +/−1 SEM).

Example 4

Figure 16A:
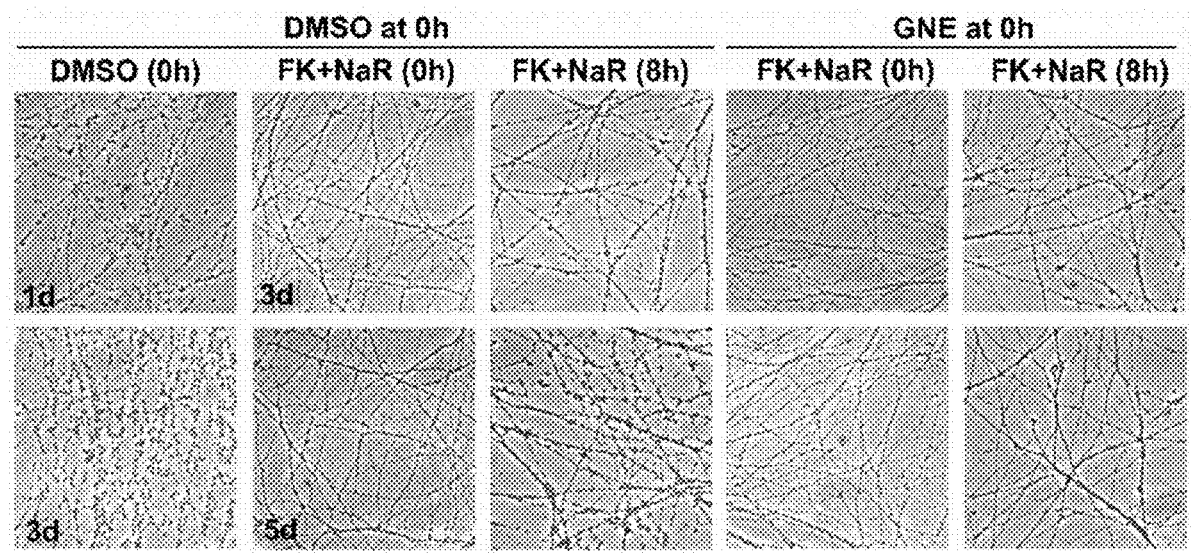
FIGS. 16A and 16B show MAPK inhibition has an additive protective effect on the dual treatment with NAMPT inhibition and NaR supplementation.
Figure 16B:
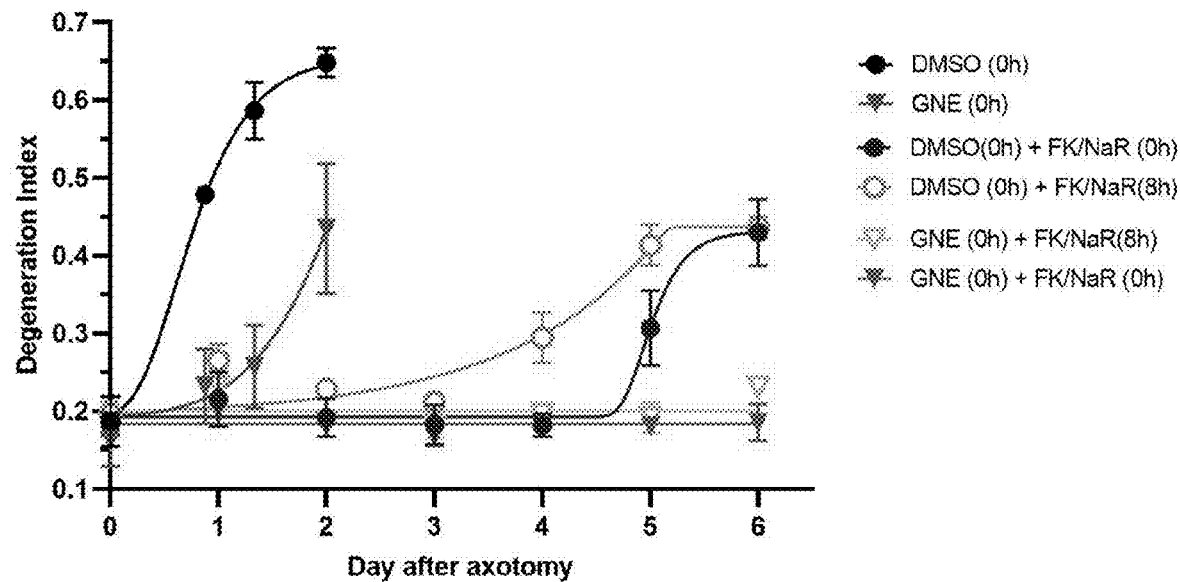

This example provides data indicating that MAPK inhibition has an additive protective effect on the dual treatment with NAMPT inhibition and NaR supplementation. Transected axons were treated at the time of injury with the DLK inhibitor GNE-3511 or vehicle (DMSO) and with the combination of FK866/NaR either at the time of injury or with an 8-hour delay. Representative micrographs are shown in FIG. 16A. Degeneration index analysis indicated long lasting protection provided by both early and delayed FK866+ NaR treatment, which was further augmented by GNE-3511. Statistical analysis of degeneration index was performed by two-way ANOVA for the effect of time (F(2.143, 17.15) =49.43, p<0.0001), treatment (F(3,8)=9.58, p=0.005), and their interactions (F(18,48)=13.99, p<0.0001) with Holm-Šidák's multiple comparisons. There were no significant differences between any of the FK+NaR groups up to day 4. However, the combined treatment of GNE with FK+NaR (whether early or delayed) provided better protection against fragmentation compared to FK+NaR treatment alone at day 6 (t(56)=6.8-8.4, p<0.0001). See FIG. 16B (error bars indicate +/−1 SEM).

Example 5

Figure 17A:
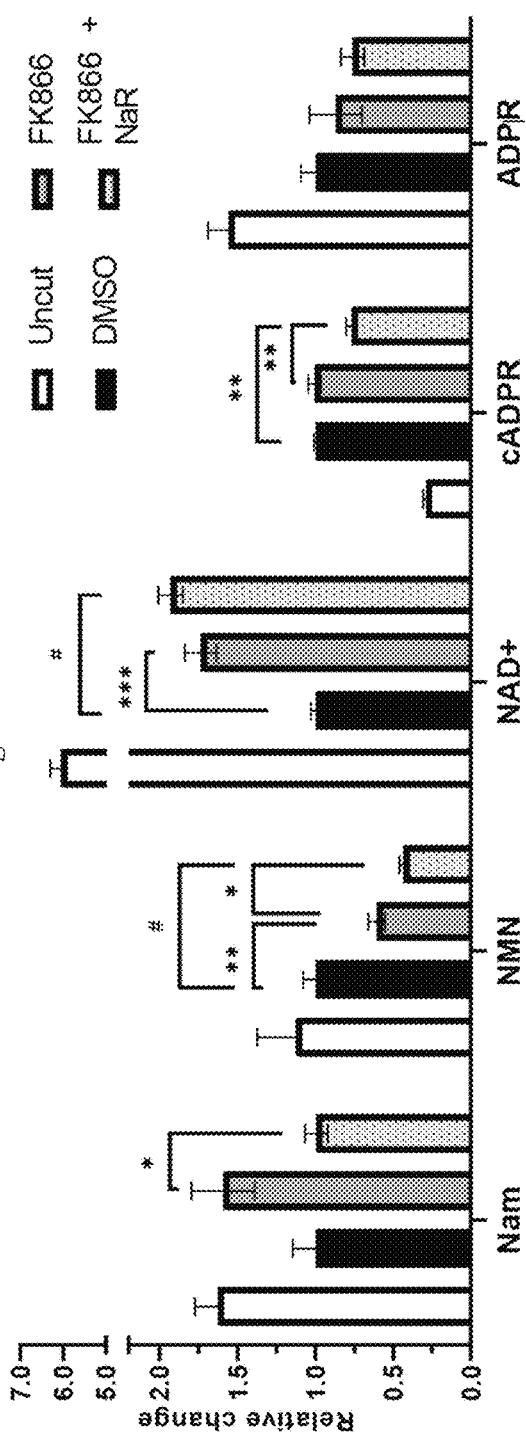
FIGS. 17A and 17B are graphs showing the supplementation of NAMPT inhibition with NaR favorably modulates the metabolic profile of axotomized axons. Axons were transected and treated with vehicle (DMSO), the NAMPT inhibitor FK866 or FK866+NaR. Axons were collected at 8 hours post axotomy for metabolite analysis.
Figure 17B:
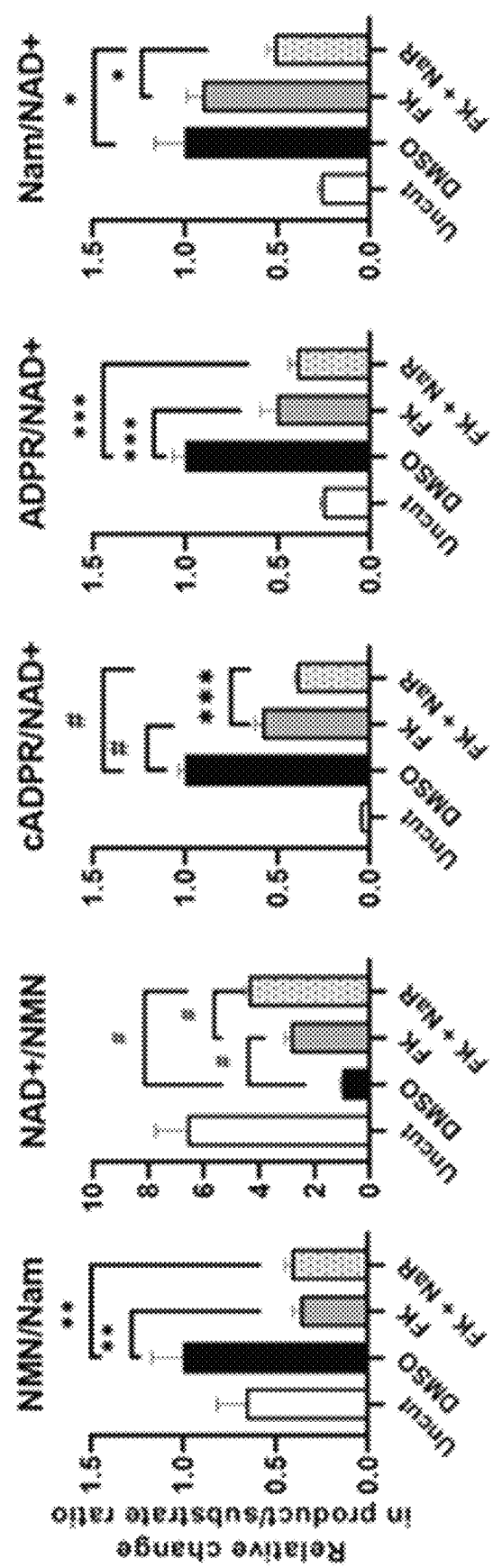

This example provides data indicating that supplementation of NAMPT inhibition with NaR favorably modulates the metabolic profile of axotomized axons. Axons were transected and treated with vehicle (DMSO), the NAMPT inhibitor FK866, or FK866+NaR. Axons were collected at 8 hours post axotomy for metabolite analysis. FIG. 17A shows relative changes in protein-normalized levels of metabolites in distal axons at 8 hours following transection and treatment at the time of injury with NAMPT inhibitor FK866 alone or in combination with NaR or vehicle (DMSO). FIG. 17B shows product/substrate ratios of key enzymatic steps. NAMPT inhibition alone or in combination with NaR suppressed NMN (t(10)=5.03, p=0.001 and t(10)=7.61, p<0.001) and protects NAD+ levels (t(10)=6.46, p=0.0001 and t(10)-8.60, p<0.0001) compared to vehicle treated transected axons, which was also reflected by reductions in the NMN/Nam 4(10)=4.44, p=0.004 and 410)=4.34, p=0.004) and increases in the NAD+/NMN ratios (t(10)=8.26, p<0.0001 and 410)=15.84, p<0.0001). Compared to NAMPT inhibition alone, NaR supplementation provided further reduction of NMN levels (410)=2.31, p=0.044) and only trend increase in NAD+ levels (t(10)=1.8, p=0.11), resulting in further increase of the NAD+/NMN ratio (t(10) =7.14, p<0.0001). Relative to vehicle treated controls, both treatments suppressed the NAD+ degrading activity (for cADPR/NAD+: t(10)=10.5, p<0.0001 and t(10)=16.03, p<0.0001) but only the combined treatment suppressed cADPR levels (t(10)=5.13, p=0.001). Statistically significant changes between treated and untreated transected axons were analyzed with one-way ANOVA and Holm-Šidák's multiple comparisons; *=p<0.05, =p<0.01, *=p<0.001, #=p<0.0001. Error bars indicate +/−1 SEM.

These data indicate that NaR synergizes with NAMPT inhibition in an unexpected way by further suppressing NMN synthesis and SARM1 activity in the first 8 hours following axonal injury and preserving NAD+ gains achieved with NAMPT inhibition.

Example 6

Figure 18A:
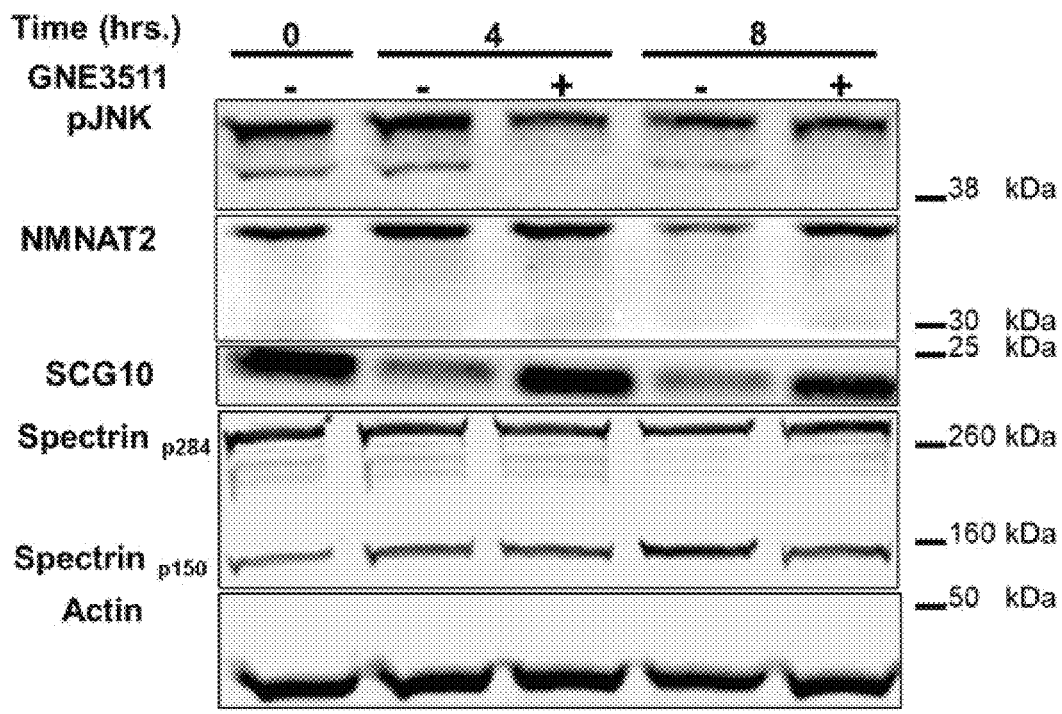
FIGS. 18A and 18B show MAPK inhibition with the DLK inhibitor GNE3511 suppresses loss of axonoprotective proteins SCG10 and NMNAT2.
Figure 18B:
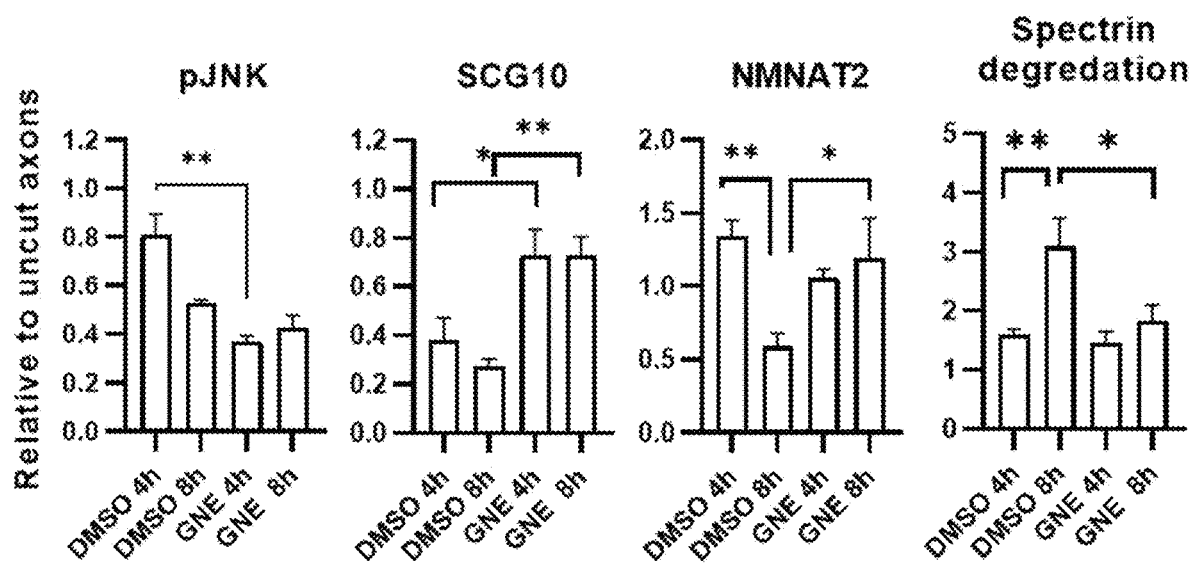

This example provides data indicating that MAPK inhibition with the DLK inhibitor GNE3511 suppresses loss of axonoprotective proteins SCG10 and NMNAT2. Western blot analysis of distal axons was performed at 4 and 8 hours after transection and treatment with the DLK inhibitor GNE3511 or vehicle (DMSO). FIG. 18A shows a representative immunoblot and FIG. 18B shows the quantification of signals normalized to actin and with reference to uninjured/untreated axon samples (n=3). GNE3511 suppressed phosphorylation of JNK at 4 hours, 45)=6.17, p=0.0005. NMNAT2 was significantly degraded between 4 and 8 hours post-axotomy (t(5)=3.5, p=0.016) in vehicle treated axons but not in the presence of GNE (t(5)=2.8, p=0.046). Similarly, GNE suppressed the injury associated degradation of SCG10 at both time points (t(5)=3.06, p=0.031; and t(5)=4.02, p=0.008 respectively) and the injury associated degradation of spectrin at 8 hours (calculated as the index of the p150 fragment to total spectrin, p284; t(5)=3.08, p=0.03).

Example 7

This example provides data indicating that MAPK inhibition alone or in combination with NAMPT inhibition and NaR supplementation favorably modulates the metabolic profile of axotomized axons. Relative changes in protein-normalized levels of metabolites in distal axons were measured at 8 hours following transection and treatment at the time of injury with the MAPK inhibitor GNE-3511, the NAMPT inhibitor FK866 in combination with NaR, or with the three compounds together. One-way ANOVA analysis with Holm-Šidák's multiple comparisons for effects between the three treatment groups revealed significant changes in NAD+(F(2,15)=44.87, p<0.0001) and NMN levels (F(2,15)=4.79, p=0.023) but not in other metabolites. Treatment with GNE resulted in greater protection of NAD+ levels compared to both FK+NaR (t(15)=9.45, p<0.001) or the triple combination (t(15)=5.25, p=0.002). The triple combination had slightly higher NMN levels compared to FK+NaR alone (415)=2.93, p=0.03). See FIG. 19A.

FIG. 19B shows relative changes in product/substrate ratios of key enzymatic steps. There were significant differences observed in the NAD+/NMN ratio F(2,15)=13.16, p=0.0005 (with GNE vs FK+NaR, 415)=4.77, p=0.0007 and GNE vs FK+NaR+GNE, t(15)=4.01, p=0.002), the cADPR/NAD+ ratio, F(2,15)=11.1 p=0.001 (with GNE vs FK+NaR, t(15)=4.66, p=0.0009 and FK+NaR+GNE vs FK+NaR, t(15) =1.73, p=0.02) and the Nam/NAD+ ratio F(2,15)=6.97, p=0.007 (with GNE vs FK+NaR, 415)=3.59, p=0.008 and GNE vs FK+NaR+GNE, t(15)=2.68, p=0.03). *=p<0.05, =p<0.01, *=p<0.001, #=p<0.0001.

Example 8

This example provides data indicating that NAMPT and MAPK inhibition with NaR supplementation suppresses axon fragmentation in human neurons. H9 human embryonic stem cells were rapidly differentiated to a cholinergic neuron phenotype using neurogenic mRNA delivery and plated in microfluidic devices. On DIV 10, neurons were transduced with a hSyn-tdTomato containing lentivirus for the fluorescent tracing of axons. On DIV 21, axons were transected with a razor blade and treated with vehicle (DMSO), FK866, or FK866+NaR+GNE3511 and imaged up to 30 hours. Axons treated with FK866+NaR+GNE3511 showed no evidence of axon fragmentation for the duration of the experiment. See FIG. 20.

REFERENCES

All references, including publications, patent applications, and patents, cited herein are hereby incorporated by reference to the same extent as if each reference were individually and specifically indicated to be incorporated by reference and were set forth in its entirety herein.
1. Frieden T R, Houry D, Baldwin G. CDC Report Congress on traumatic brain injury in the United States: Epidemiology and Rehabilitation, vol. 2015; 2015.
2. Adams J H, Murray M F. Atlas of post-mortem techniques in neuropathology, vol. 1982. Cambridge: Cambridge University Press; 1982.
3. Blumbergs P C, Jones N R, North J B. Diffuse axonal injury in head trauma. J Neurol Neurosurg Psychiatry. 1989; 52:838-41.
4. Blumbergs P C, Scott G, Manavis J, Wainwright H, Simpson D A, Mclean A J. Staining of amyloid precursor protein to study axonal damage in mild head-injury. Lancet. 1994; 344(8929): 1055-6.
5. Mittl R L, Grossman R I, Hiehle J F, Hurst R W, Kauder D R, Gennarelli T A, et al. Prevalence of M R evidence of diffuse axonal injury in patients with mild head injury and normal head C T findings. AJNR Am J Neuroradiol. 1994; 15(8):1583-9.
6. Strich S J. Diffuse degeneration of the cerebral white matter in severe dementia following head injury. J Neurol Neurosurg Psychiatry. 1956; 19: 163-85.
7. Foda M A A, Marmarou A. A New Model of Diffuse Brain Injury in Rats 0.2.Morphological Characterization. J Neurosurg. 1994; 80(2):301-13.
8. Marmarou A, Foda MAA, Vandenbrink W, Campbell J, Kita H, Demetriadou K. A New Model of Diffuse Brain Injury in Rats 0.1. Pathophysiology and Biomechanics. J Neurosurg. 1994; 80(2):291-300.
9. Povlishock J T, Erb D E, Astruc J. Axonal response to traumatic brain injury: reactive axonal change, deafferentation, and neuroplasticity. J Neurotrauma. 1992; 9(Suppl. 1):S189-200.
10. Povlishock J T, Marmarou A, McIntosh T, Trojanowski J Q, Moroi J. Impact acceleration injury in the rat: evidence for focal axolemmal change and related neurofilament sidearm alteration. J Neuropathol Exp Neurol. 1997; 56(4):347-59.
11. Xu L, Nguyen J V, Lehar M, Menon A, Rha E, Arena J, et al. Repetitive mild traumatic brain injury with impact acceleration in the mouse: multifocal axonopathy, neuroinflammation, and neurodegeneration in the visual system. Exp Neurol. 2016; 275(Pt 3):436-49.
12. Ziogas N K, Koliatsos V E. Primary traumatic Axonopathy in mice subjected to impact acceleration: a reappraisal of pathology and mechanisms with high-resolution anatomical methods. J Neurosci. 2018; 38(16):4031-47.
13. Bricker-Anthony C, Rex T S. Neurodegeneration and vision loss after mild blunt trauma in the C57Bl/6 and DBA/2J mouse. PLoS One. 2015; 10(7): e0131921.
14. Koliatsos V E, Cernak I, Xu L, Song Y, Savonenko A, Crain B J, et al. A mouse model of blast injury to brain: initial pathological, neuropathological, and behavioral characterization. J Neuropathol Exp Neurol. 2011; 70(5): 399-416.
15. Wang J, Hamm R J, Povlishock J T. Traumatic axonal injury in the optic nerve: evidence for axonal swelling, disconnection, dieback, and reorganization. J Neurotrauma. 2011; 28(7):1185-98.
16. Fernandes K A, Harder J M, John S W, Shrager P, Libby R T. DLK-dependent signaling is important for somal but not axonal degeneration of retinal ganglion cells following axonal injury. Neurobiol Dis. 2014; 69:108-16.
17. Watkins T A, Wang B, Huntwork-Rodriguez S, Yang J, Jiang Z, Eastham-Anderson J, et al. DLK initiates a transcriptional program that couples apoptotic and regenerative responses to axonal injury. Proc Natl Acad Sci USA. 2013; 110(10):4039-44.
18. Welsbie D S, Mitchell K L, Jaskula-Ranga V, Sluch V M, Yang Z, Kim J, et al. Enhanced functional genomic screening identifies novel mediators of dual Leucine zipper kinase-dependent injury signaling in neurons. Neuron. 2017; 94(6):1142-54.
19. Welsbie D S, Yang Z, Ge Y, Mitchell K L, Zhou X, Martin S E, et al. Functional genomic screening identifies dual leucine zipper kinase as a key mediator of retinal ganglion cell death. Proc Natl Acad Sci USA. 2013; 110(10):4045-50.
20. Holland S M, Collura K M, Ketschek A, Noma K, Ferguson T A, Jin Y, et al. Palmitoylation controls DLK localization, interactions and activity to ensure effective axonal injury signaling. Proc Natl Acad Sci USA. 2016; 113(3):763-8.
21. Xiong X, Wang X, Ewanek R, Bhat P, DiAntonio A, Collins C A. Protein turnover of the Wallenda/DLK kinase regulates a retrograde response to axonal injury. J Cell Biol. 2010; 191(1):211-23.
22. Miller B R, Press C, Daniels R W, Sasaki Y, Milbrandt J, DiAntonio A. A dual leucine kinase-dependent axon self-destruction program promotes Wallerian degeneration. Nat Neurosci. 2009; 12(4):387-9.
23. Summers D W, Milbrandt J, DiAntonio A. Palmitoylation enables MAPK-dependent proteostasis of axon survival factors. Proc Natl Acad Sci USA. 2018; 115(37): E8746-E54.
24. Yang J, Wu Z, Renier N, Simon D J, Uryu K, Park D S, et al. Pathological axonal death through a MAPK cascade that triggers a local energy deficit. Cell. 2015; 160(1-2): 161-76.
25. Arevalo M A, Azcoitia I, Garcia-Segura L M. The neuroprotective actions of oestradiol and oestrogen receptors. Nat Rev Neurosci. 2015; 16(1):17-29.
26. Green P S, Simpkins J W. Neuroprotective effects of estrogens: potential mechanisms of action. Int J Dev Neurosci. 2000; 18(4-5):347-58.
27. Mollayeva T, Mollayeva S, Colantonio A. Traumatic brain injury: sex, gender and intersecting vulnerabilities. Nat Rev Neurol. 2018; 14(12):711-22.
28. Raghava N, Das B C, Ray S K. Neuroprotective effects of estrogen in CNS injuries: insights from animal models. Neurosci Neuroecon. 2017; 6:15-29.
29. Suzuki S, Brown C M, Wise P M. Mechanisms of neuroprotection by estrogen. Endocrine. 2006; 29(2):209-15.
30. Karaman M W, Herrgard S, Treiber D K, Gallant P, Atteridge C E, Campbell B T, et al. A quantitative analysis of kinase inhibitor selectivity. Nat Biotechnol. 2008; 26(1):127-32.
31. Tang S C, Lagas J S, Lankheet N A, Poller B, Hillebrand M J, Rosing H, et al. Brain accumulation of sunitinib is restricted by P-glycoprotein (ABCB1) and breast cancer resistance protein (ABCG2) and can be enhanced by oral elacridar and sunitinib coadministration. Int J Cancer. 2012; 130(1):223-33.
32. Levkovitch-Verbin H. Animal models of optic nerve diseases. Eye (Lond). 2004; 18(11):1066-74.
33. Lobato R D. Historical vignette of Caj al's work "degeneration and regeneration of the nervous system" with a reflection of the author. Neurocirugia (Astur). 2008; 19(5):456-68.
34. Villegas-Perez M P, Vidal-Sanz M, Rasminsky M, Bray G M, Aguayo A J. Rapid and protracted phases of retinal ganglion cell loss follow axotomy in the optic nerve of adult rats. J Neurobiol. 1993; 24(1):23-36.
35. Ghosh A S, Wang B, Pozniak C D, Chen M, Watts R J, Lewcock J W. DLK induces developmental neuronal degeneration via selective regulation of proapoptotic JNK activity. J Cell Biol. 2011; 194(5):751-64.
36. Shen Q, Hiebert J B, Hartwell J, Thimmesch A R, Pierce J D. Systematic review of traumatic brain injury and the impact of antioxidant therapy on clinical outcomes. Worldviews Evid-Based Nurs. 2016; 13(5):380-9.
37. Buki A, Povlishock J T. All roads lead to disconnection? Traumatic axonal injury revisited. Acta Neurochir. 2006; 148(2):181-93.
38. Shin J E, Miller B R, Babetto E, Cho Y, Sasaki Y, Qayum S, et al. SCG10 is a JNK target in the axonal degeneration pathway. Proc Natl Acad Sci USA. 2012; 109(52):E3696-705.
39. Gilley J, Coleman 1V11$^3$. Endogenous Nmnat2 is an essential survival factor for maintenance of healthy axons. PLoS Biol. 2010; 8(1):e1000300.
40. Lim J H, Stafford B K, Nguyen P L, Lien B V, Wang C, Zukor K, et al. Neural activity promotes long-distance, target-specific regeneration of adult retinal axons. Nat Neurosci. 2016; 19(8):1073-84.
41. Jakobs T C, Libby R T, Ben Y, John S W, Masland R H. Retinal ganglion cell degeneration is topological but not cell type specific in DBA/2J mice. J Cell Biol. 2005; 171(2):313-25.
42. Libby R T, Li Y, Savinova O V, Barter J, Smith R S, Nickells R W, et al. Susceptibility to neurodegeneration in a glaucoma is modified by Bax gene dosage. PLoS Genet. 2005; 1(1):17-26.
43. Whitmore A V, Libby R T, John S W. Glaucoma: thinking in new ways—a role for autonomous axonal self-destruction and other compartmentalized processes? Prog Retin Eye Res. 2005; 24(6):639-62.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention, and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for inhibiting or preventing neuron injury or death, which method consists of contacting the one or more neurons with an effective amount of:
   a small molecule that modulates one or more mitogen-activated kinase kinase kinases (MAP3Ks); and
   a small molecule that modulates a nicotinamide phosphoribosyltransferase (NAMPT).

2. The method of claim 1, wherein the contacting is simultaneous, sequential, or a combination thereof.

3. The method of claim 1, wherein the one or more MAP3Ks is dual leucine zipper kinase (DLK) and/or leucine zipper kinase (LZK).

4. The method of claim 1, wherein the small molecule that modulates one or more MAP3Ks is selected from sunitinib, GNE-3511, CEP-1347, and CEP-11004.

5. The method of claim 1, wherein the small molecule that modulates a NAMPT is FK-866.

6. The method of claim 5, which consists of contacting one or more neurons with GNE-3511 and FK-866.

7. The method of claim 1, wherein the one or more neurons are in vivo.

8. The method of claim 7, wherein the contacting consists of administering the small molecule that modulates one or more mitogen-activated kinase kinase kinases (MAP3Ks) and the small molecule that modulates a nicotinamide phosphoribosyltransferase (NAMPT) to a subject.

9. The method of claim 8, wherein the subject has experienced a traumatic brain injury.

10. The method of claim 1, wherein the inhibiting or preventing neuron injury or death comprises suppression of axon fragmentation, suppression of the loss of axonoprotective proteins, modulation of the metabolic profile of the one or more neurons, reduction of axonal degradation and/or synaptic degradation, or a combination thereof.

11. A method of treating or preventing a neuropathy or axonopathy in a subject in need thereof, the method consisting of administering to the subject an effective amount of:
    a small molecule that modulates one or more mitogen-activated kinase kinase kinases (MAP3Ks); and
    a small molecule that modulates a nicotinamide phosphoribosyltransferase (NAMPT).

12. The method of claim 11, wherein the administering is simultaneous, sequential, or a combination thereof.

13. The method of claim 11, wherein the small molecule that modulates one or more MAP3Ks is selected from sunitinib, GNE-3511, CEP-1347, and CEP-11004.

14. The method of claim 11, wherein the small molecule that modulates a NAMPT is FK-866.

15. The method of claim 14, which consists of administering GNE-3511 and FK-866 to the subject.

16. The method of claim 11, wherein the neuropathy or axonopathy is hereditary or congenital or associated with neurodegenerative disease, motor neuron disease, neoplasia, endocrine disorder, metabolic disease, nutritional deficiency, atherosclerosis, an autoimmune disease, mechanical injury, chemical or drug-induced injury, thermal injury, radiation injury, nerve compression, retinal or optic nerve disorder, mitochondrial dysfunction, progressive dementia demyelinating diseases ischemia and/or stroke infectious disease; or inflammatory disease.

17. The method of claim 11, wherein the neuropathy or axonopathy is caused by a traumatic brain injury.

18. The method of claim 16, wherein the onset of treating is within one to ten hours of injury.

* * * * *